(12) United States Patent
Anand et al.

(10) Patent No.: US 11,160,911 B2
(45) Date of Patent: Nov. 2, 2021

(54) ELECTROKINETIC ROUTE TO A WEARABLE DEVICE FOR KIDNEY DISEASE MANAGEMENT

(71) Applicant: Iowa State University Research Foundation, Inc., Ames, IA (US)

(72) Inventors: Robbyn K. Anand, Ames, IA (US); Beatrise Berzina, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 559 days.

(21) Appl. No.: 16/171,892

(22) Filed: Oct. 26, 2018

(65) Prior Publication Data

US 2019/0125951 A1 May 2, 2019

Related U.S. Application Data

(60) Provisional application No. 62/577,553, filed on Oct. 26, 2017.

(51) Int. Cl.
*A61M 1/16* (2006.01)
*A61M 1/34* (2006.01)
*B01D 61/24* (2006.01)

(52) U.S. Cl.
CPC ........ *A61M 1/1656* (2013.01); *A61M 1/1603* (2014.02); *A61M 1/1672* (2014.02); *A61M 1/1678* (2013.01); *A61M 1/3486* (2014.02); *A61M 2202/0415* (2013.01); *A61M 2202/0488* (2013.01); *A61M 2209/088* (2013.01);
(Continued)

(58) Field of Classification Search
CPC .... A61M 1/1656; A61M 1/16; A61M 1/1603; A61M 1/1654; A61M 1/1668; A61M 1/1672; A61M 1/1678; A61M 1/3486; A61M 2202/0415; A61M 2202/0488;
(Continued)

(56) References Cited

U.S. PATENT DOCUMENTS 8,137,299 B2 3/2012 Gura et al.
8,501,009 B2 * 8/2013 Peterson ................. C02F 1/001
210/652
(Continued)

OTHER PUBLICATIONS

Berzina et al., "Electrokinetic Separation of Neutral Species from Human Blood Plasma: Therapeutic and Clinical Application", Gordon Research Conference, poster, Jun. 4, 2017.
(Continued)

*Primary Examiner* — Philip R Wiest
(74) *Attorney, Agent, or Firm* — McKee, Voorhees & Sease, PLC

(57) ABSTRACT

A portable device for removal of metabolic waste from the blood of patient having kidney disease or in need of hemodialysis is provided. Methods of hemodialysis employing the portable device beneficially obtain a dialysate by electrokinetic means from excess fluid in the peripheral blood of the patient in need thereof. The methods employ a branched microfluidic channel for the use of ion concentration polarization to separate charged from neutral species in blood to obtain the dialysate for undergoing hemodialysis. Beneficially the methods and device are resistant to biofouling, remove the need for a dialysate and/or dialysate reservoir, and provide a disposable, wearable device.

27 Claims, 14 Drawing Sheets
(13 of 14 Drawing Sheet(s) Filed in Color)

(52) U.S. Cl.
CPC ... *A61M 2230/20* (2013.01); *A61M 2230/201* (2013.01); *B01D 61/243* (2013.01)

(58) Field of Classification Search
CPC ........ A61M 2209/088; A61M 2230/20; A61M 2230/201; B01D 31/243
See application file for complete search history.

(56) References Cited

U.S. PATENT DOCUMENTS

| | | | |
|---|---|---|---|
| 9,402,941 B2 | 8/2016 | Rambod et al. | |
| 2011/0192796 A1* | 8/2011 | Smejtek | F28D 9/0093 210/652 |
| 2013/0102948 A1* | 4/2013 | Reich | A61M 1/3482 604/6.09 |
| 2014/0183046 A1* | 7/2014 | Crooks | C02F 1/4604 204/554 |

OTHER PUBLICATIONS

Perdue et al., "Bipolar Electrode Focusing: The Effect of Current and Electric Field on Concentration Enrichment", Analytical Chemistry, vol. 81, No. 24, pp. 10149-10155, Dec. 15, 2009.
Anand et al., "Bipolar Electrode Focusing: Faradaic Ion Concentration Polarization", Analytical Chemistry, vol. 83, pp. 2351-2358, 2011.
Nakashima et al., "Blood plasma separation and extraction from a minute amount of blood using dielectrophoretic and capillary forces", Sensors and Actuators, B 145, pp. 561-569, 2010.
Song et al., "Concurrent DNA preconcentration and separation in bipolar electrode-based microfluidic device", Analytical Methods, vol. 7, No. 4, pp. 1273-1279, Feb. 21, 2015.
Shafiee et al., "Contactless dielectrophoresis: a new technique for cell manipulation", Biomed Microdevices, 11, pp. 997-1006, May 5, 2009.
Cheow et al., "Detecting Kinase Activities from Single Cell Lysate Using Concentration-Enhanced Mobility Shift Assay", Analytical Chemistry, 86, pp. 7455-7462, 2014.
Kim et al., "Direct seawater desalination by ion concentration polarization", Nature Nanotechnology, vol. 5, pp. 297-301, Apr. 2010.
Knust et al., "Dual-channel bipolar electrode focusing: simultaneous separation and enrichment of both anions and nations", 12, pp. 4107-4114, 2012.
Knust et al., "Electrochemically-Mediated Seawater Desalination", Angew Chem Int Ed Engl., 52(31), pp. 8107-8110, Jul. 29, 2013.
Sheridan et al., "Enrichment of Cations via Bipolar Electrode Focusing", Analytical Chemistry, 84, pp. 7393-7399, Aug. 14, 2012.
Ronco et al., "The future of the artificial kidney: moving towards wearable and miniaturized devices", Revista Nefrologia, 31(1), pp. 9-16, 2011.
Kim et al., "Partial desalination of hypersaline brine by lab-scale ion concentration polarization device", Elsevier, pp. 20-31, Mar. 7, 2017.
Kim et al., "Purification of High Salinity Brine by Multi-Stage Ion Concentration Polarization Desalination", Scientific Reports, pp. 1-12, Aug. 22, 2016.
Kwak et al., "Enhanced Salt Removal by Unipolar Ion Conduction in Ion Concentration Polarization Desalination", Scientific Reports, pp. 1-11, May 9, 2016.
Choi et al., "Integrated pretreatment and desalination by electrocoagulation (EC)-ion concentration polarization (ICP) hybrid", The Royal Society of Chemistry, pp. 2076-2084, May 12, 2017.
Wanner et al., "The heart and vascular system in dialysis", vol. 388, pp. 276-284, Jul. 16, 2016.
Mohammadi et al., "Hydrodynamic and direct-current insulator-based dielectrophoresis (H-DC-iDEP) microfluidic blood plasma separation", Anal Bioanal. Chem., 407, pp. 4733-4744, Apr. 30, 2015.
Kim et al., "Ion concentration polarization in a single and open microchannel induced by a surface-patterned perm-selective film", Analyst, 138, pp. 1370-1378, 2013.
Yan et al., "Isolating plasma from blood using a dielectrophoresis-active hydrophoretic device", Lab Chip, 14, pp. 2993-3003, Mar. 26, 2014.
Kim et al., "Ion Concentration Polarization by Bifurcated Current Path", Scientific Reports, pp. 1-12, Jul. 11, 2017.
Knust et al., "Electrochemically Mediated Seawater Desalination", Angew. Chem. Int. Ed., 52, pp. 8107-8110, 2013.
Ko et al., "Massively parallel concentration device for multiplexed immunoassays", Lab Chip, 11, pp. 1351-1358, Jan. 24, 2011.
Kim et al., "Microelectromechanical Systems and Nephrology: The Next Frontier in Renal Replacement Technology", Advances in Chronic Kidney Disease, vol. 20, No. 6, pp. 516-535, Nov. 2013.
Song et al., "Nafion Film Based Micro-nanofluidic Device for Concurrent DNA Preconcentration and Separation in Free Solution", Microfluid Nanofluidics, 17(4), pp. 693-699, Oct. 1, 2014.
MacDonald et al., "Out-of-plane ion concentration polarization for scalable water desalination", Lab Chip, 14, pp. 581-685, 2014.
McDonald et al., "Poly(dimethylsiloxane) as a Material for Fabricating Microfluidic Devices", Accounts of Chemical Research, vol_.35, No. 7, pp. 491-499, Jul. 2002.
Li et al., "Recent advancements in ion concentration polarization", Analyst, 141, 3496-3510, Mar. 3, 2016.
Kim et al., "Direct seawater desalination by ion concentration polarization", Nature Nanotechnology, vol. 5, pp. 297-301, Mar. 21, 2010.
Andersen et al., "Spatiotemporal pH Dynamics in Concentration Polarization near Ion-Selective Membranes", Langmuir, 30, pp. 7902-7912, Jun. 3, 2014.
Kim et al., "Stabilization of ion concentration polarization layer using micro fin structure for high-throughput applications", Nanoscale, 9, pp. 3466-3475, Feb. 3, 2017.
Rastogi et al., "Technological Advances in Renal Replacement Therapy: Five Years and Beyond", American Society of Nephrology, 4, pp. S132-S136, 2009.
Milne et al., "Tunable Donnan Potential and Electrokinetic Flow in a Biomimetic Gated Nanochannel with pH-Regulated Polyelectrolyte Brushes", Journal of Physical Chemistry, 118, pp. 19806-19813, Aug. 5, 2014.
Gura et al., "A wearable artificial kidney for patients with end-stage renal disease", JCI Insight, pp. 1-15, Jun. 2, 2016.
Xu, Tongwen, "Ion exchange membranes: State of their development and perspective", Journal of Membrane Science, 263, pp. 1-29, Aug. 15, 2005.
Jones et al., "Keeping Kidneys", Bull World Health Organ, 90, pp. 718-719, Oct. 1, 2012.
Chen, Chia-Hung et al., "Buffer-free integrative nanofluidic device for real-time continuous flow bioassays by ion concentration polarization", The Royal Society of Chemistry, Lab Chip, vol. 18, No. 4, 574-584, Feb. 21, 2018.
Kim, Wanseok et al., "Nanoelectrokinetic Purification Device for a Continuous Peritoneal Dialysate Recycler", MEMS 2017, Las Vegas, NV, USA, 319-322, Jan. 22-26, 2017.

* cited by examiner

Scheme 2

ELECTROKINETIC ROUTE TO A WEARABLE DEVICE FOR KIDNEY DISEASE MANAGEMENT

CROSS-REFERENCE TO RELATED APPLICATIONS

This application claims priority under 35 U.S.C. § 119 to provisional application Ser. No. 62/577,553, filed Oct. 26, 2017, herein incorporated by reference in its entirety.

FIELD OF THE INVENTION

The present invention relates generally to a device for removal of metabolic waste from the blood of a subject in need thereof without the use of a dialysate. The invention further includes methods of creating a dialysate by electrokinetic means from excess fluid in the peripheral blood of a subject through use of a branched microfluidic channel employing ion concentration polarization to separate charged from neutral species in blood. Thereafter, the dialysate contacts a hemodialysis membrane. Beneficially the methods and device are resistant to biofouling, remove the need for a dialysate and/or dialysate reservoir, and provide a disposable, wearable device.

BACKGROUND INFORMATION

According to the World Health Organization, more than 70,000 people per year receive a kidney transplant—and most importantly, this number represents only 10% of the total number on the waiting list. The remaining patients require intermittent treatment by either peritoneal dialysis or hemodialysis several times per week. Between dialysis sessions, patients suffer from fluid retention and a gradual increase in the concentration of metabolic waste products in the blood. In the short term, fluid retention leads to weight gain, edema, shortness of breath, and rapid pulse. However, repeated episodes of fluid retention may cause permanent damage to the heart and lungs. As a result, cardiac failure is a leading cause of mortality in dialysis patients. These health risks associated with intermittent therapy are
clear indication that slow continuous dialysis would greatly improve quality of life and prognosis for patients with kidney failure.

In response to this need, there has been significant advancement towards miniaturized wearable devices for the removal of metabolic waste from the blood. For example, the wearable artificial kidney (WAK) is the first truly portable hemodialysis device, having all components attached to a belt (similar in size to a back brace). The WAK was shown in its first clinical trials to successfully maintain blood components at healthy levels over a 24-hour period. Another system, called the Vincenza wearable artificial kidney for peritoneal dialysis (ViWAK PD) consumes a reduced dialysate volume based on sorbent-assisted regeneration. Despite these major advancements, the systems are still heavy and cumbersome.

Due to the need for miniaturization, microfluidic technologies are being incorporated into artificial transplantable kidneys and dialysis devices. For example, a miniaturized hemodialysis module that uses a lithographically patterned nanomembrane to significantly increase transmembrane diffusion and thereby decrease dialyzer size has been developed. To remove the need for dialysate, there has been development of an implantable 'human nephron filter' that employs a multi-membrane system to mimic the function of the glomerulus and tubules functions in the nephron. Currently, the membrane materials, which must provide specific interactions with small solutes, are under development.

Despite significant progress in kidney disease management, the requirement for dialysate remains to be the primary barrier to the creation of a wearable device capable of continuously cleansing the blood of metabolic waste.

Accordingly, it is an objective of the claimed invention to develop a device and methods for slow, continuous hemodialysis without the requirement of a large reservoir of dialysate. In a preferred objective, the methods and device employ ion concentration polarization to continuously separate excess fluid from uremic blood and blood plasma, providing resultant purified fluids that can be employed as an in-line source of dialysate.

A further object of the invention is to develop an electrokinetic means of producing dialysate from excess fluid extent in the peripheral blood of patients undergoing therapy while retaining essential components of blood, such as serum albumin. In a preferred objective, the methods and device use electrophoretic and electroosmotic transport across membranes to enhance waste clearance with enhanced efficiency to allow use of a patient's blood plasma as a source of dialysate.

A further object of the invention is to provide a method for hemodialysis that does not cause damage to proteins and/or result in biofouling of membranes employed in the device.

Other objects, advantages and features of the present invention will become apparent from the following specification taken in conjunction with the accompanying drawings.

SUMMARY OF THE INVENTION

An advantage of the invention is a disposable, wearable device for hemodialysis. It is an advantage of the present invention that the methods and device source fluid from blood that can be utilized as a patient-derived dialysate to accept metabolic waste during hemodialysis. Beneficially, the methods are analogous to the removal of waste by a healthy human kidney, which sources excess fluid from the blood to accept waste.

In an embodiment, the present invention provides methods for treating kidney disease by hemodialysis and devices suitable for use with the treatment of a bodily fluid.

In an embodiment, the present invention includes a method for hemodialysis comprising: removing neutral compounds from blood plasma of a subject in need of hemodialysis by ion concentration polarization; obtaining fluid from the blood plasma containing the neutral compounds to source as a subject-derived dialysate; and using the dialysate to accept metabolic waste during hemodialysis.

In an embodiment a method for treating kidney disease by hemodialysis includes providing a subject in need of hemodialysis with a branched, flow-through microfluidic device, applying a charge to the device, separating neutral compounds from charged compounds in the subject's blood plasma at a rate of about 0.01 to about 50 mL/minute to generate two streams by ion concentration polarization, wherein the first stream is a neutral stream and the second stream is a charged stream, generating a fluid dialysate comprising the neutral stream from the subject's blood plasma, and contacting the dialysate and the second stream with a hemodialysis membrane to accept metabolic waste from the subject in need thereof.

In a further embodiment, the invention provides a device for use with the treatment of a bodily fluid, comprising a microfluidic member including an inlet channel terminating at a junction including a first branch and a second branch extending from the junction; and a charged ion permselective membrane positioned generally at or near the junction, wherein the membrane directs charged particles into the first branch and substantially neutral fluid into the second branch; and wherein the substantially neutral fluid is used as a natural dialysate for the treatment of the bodily fluid.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows channels with voltage applied; and FIG. 3B shows channels without voltage applied. When the voltage is applied to the membrane, the dye-linked albumin is redirected into the upper branched channel (FIG. 3A), whereas the dye-linked albumin flows equally to both outlets without voltage applied (FIG. 3B).

In FIG. 16A a charged species (red, Texas Red) is redirected in the upper branch under an applied voltage of 60.0 V, while in FIG. 16B a neutral (green, BODIPY) is not affected by the electric field.

Figure 1A:
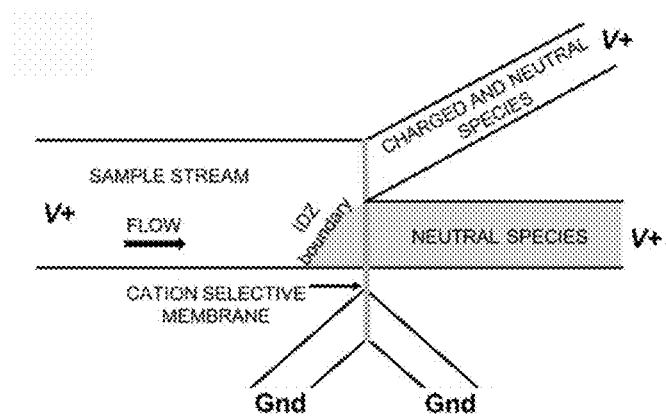
FIG. 1A shows an application of ion concentration polarization in a device for microfluidic desalination, applying a branched scheme with a cation selective membrane.

Various embodiments of the methods and device will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF INVENTION

The present invention relates to methods and device for hemodialysis without the use of a dialysate. The methods and device have many advantages over conventional hemodialysis. For example, the methods allow for the use of a disposable, wearable device providing slow, continuous hemodialysis without the requirement of a large reservoir of dialysate.

In an aspect, the methods and device provide for the removal of neutral compounds (e.g. water and small neutral molecules) from blood plasma by ion concentration polarization (ICP) in a branched microchannel.

ICP is the simultaneous enrichment and depletion of ions at opposing ends of an ion permselective membrane or bipolar electrode when an electrical voltage is applied across it. In ICP, the electric field gradient present at the boundary of the ion depletion zone (IDZ) has been employed for concentration enrichment and separation of charged species. The application of ICP methods and device for hemodialysis are unexpectedly well-suited for a branched, flow-through microfluidic device according to embodiments of the invention. Beneficially, for the methods and device of the present disclosure, the separation is employed to source fluid from blood that can be utilized downstream, as patient-derived dialysate, to accept metabolic waste during hemodialysis.

Figure 1B:
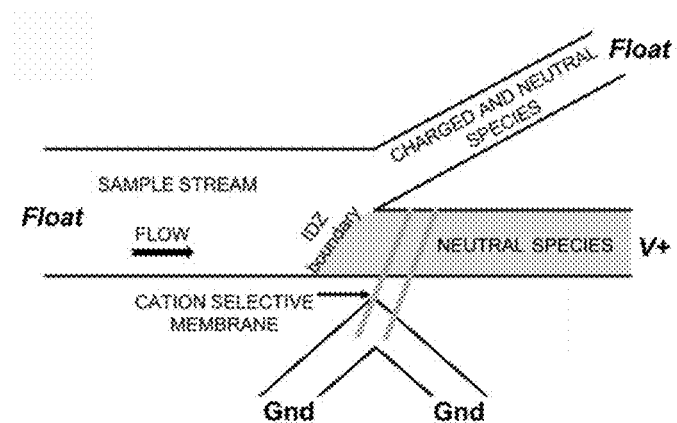
FIG. 1B shows a modified configuration according to embodiments of the invention for use in blood plasma having a distinct placement of the membrane and the driving electrodes, where the positive voltage is not applied in all three reservoirs (inlet and both outlets as shown in FIG. 1A) and instead the positive voltage is applied only in one outlet (neutral species branch outlet) with the other outlet and the inlet have a floating potential (no driving electrode).

For example, ICP has been used to separate charged from neutral species in desalination processes. FIG. 1A shows an application of ion concentration polarization in a device for microfluidic desalination. The figures show a branched scheme channel connected to an auxiliary channel at a junction, such as a nanoporous membrane (see, e.g., CATION SELECTIVE MEMBRANE, Scheme 1a) that facilitates selective charge transport. To achieve separation, the sample stream is flowed into the main (branched) channel (left to right, Scheme 1a) and a driving voltage (V+) is applied between this main channel and the auxiliary channel. If the membrane selectively permits cations, then an IDZ forms in the main channel near the micro/nano junction. When employed for desalination, it was shown that charged species are repelled from the IDZ and redirected into the upper microchannel branch ('brine stream') while neutral species are unaffected, passing equally into both branches. Accordingly, embodiments of the invention are embodied in the exemplary FIG. 1B which is a modified device configuration that has been adapted for sourcing fluid from blood plasma.

While this process and the configuration depicted in FIG. 1A has been used in desalination processes, as will be understood, aspects of the various embodiments of the invention disclosed herein include the use of ICP for human-related purposes, such as, but not limited to, in dialysis processes to allow for mobile dialysis that eliminates or otherwise mitigates the need for a separate dialysate.

The embodiments of this invention are not limited to particular methods and devices, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural references unless the context clearly indicates otherwise. Further, all units, prefixes, and symbols may be denoted in their SI accepted form. Numeric ranges recited within the specification are inclusive of the numbers defining the range and include each integer within the defined range.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation; the preferred materials and methods are described herein. In describing and claiming the embodiments of the present invention, the headings provided are not limitations on the embodiments of the invention and the following terminology will be used in accordance with the definitions set out below.

Electrokinetic Methods

The methods described herein employ ion concentration polarization (ICP) for the simultaneous enrichment and depletion of ions at opposing ends of an ion permselective membrane or bipolar electrode when an electrical voltage is applied across it. In general, the membranes are nanoporous and have fixed charges along the pore surface that permit counter-ions and exclude co-ions such that only counter-ions migrate through the membrane when a voltage is applied across the membrane. For example, Nafion has been known to provide such properties. Nafion is a sulfonated tetrafluoroethylene based fluoropolymer-copolymer. The pores extant in Nafion present sulfonate moieties (anionic) and at the pore surface, the negative electrostatic potential results in an electrical double layer of mobile cations. Due to the close proximity (approx. 4 nm) of the pore surfaces to each other, the electrical double layers overlap, and anions are completely excluded from the pores (a phenomenon termed Donnan exclusion). Donnan exclusion (whether partial or complete) can be achieved with a wide range of materials having constrictions (pores, channels, or interstitial spaces, e.g., between micrometer-scale beads) on the order of 10 microns or less. In other embodiments, additional biocompatible porous membranes, coated bead beds and bipolar electrodes (BPE) could also be employed to facilitate ICP.

In an aspect, the device employing the ICP is initially primed with a buffer such as phosphate, carbonate, Tris, HEPES, or other biocompatible buffering agent with ionic strength on an order of magnitude of 10 mM to 100 mM and within 1.0 unit of pH to that of blood (pH 7.4). In another aspect, the device can be coated to ensure anti-fouling, including any non-specific adsorption onto the walls thereof.

In an aspect, the electrical voltage is applied across the ion permselective membrane or bipolar electrode before any blood plasma is in contact with the membrane or bipolar electrode. Exemplary ion permselective membranes include, for example, Nafion membranes.

Figure 2:
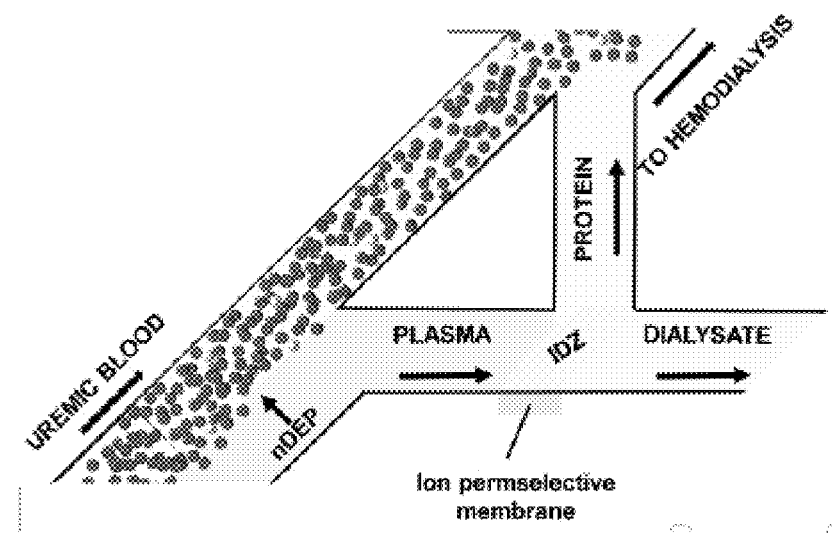
FIG. 2 shows application of ICP-based separation of blood plasma for use in the devices described herein.

Once the plasma undergoes ICP there is a separation into two streams within a branched microchannel. According to embodiments the separation is based on charge as opposed to size. The first stream is a charged stream (labeled 'protein' in FIG. 2 depiction), which is the fraction of the plasma containing charged species that are recombined with the cell containing fraction of the subject or patient's blood that will ultimately undergo hemodialysis downstream. In an embodiment, such charged species also include all proteins, such as human serum albumin (66.5 kDa). The second stream is a neutral stream (labeled 'dialysate' in FIG. 2 depiction), which is thereafter used as dialysate.

In an embodiment, the ICP separation is highly efficient due to separation by charge. In an embodiment, at least 90% separation efficiency, or at least 95% separation efficiency is achieved.

The use of ICP in contact with blood plasma beneficially forms a stable ion depletion zone (IDZ) for continuous separation of neutral species in blood plasma. The IDZ provides a highly locally enhanced electric field, which excludes (repels) all charged species. As a result of repelling charged species, such as proteins, away from its surface, the methods do not result in biofouling of the membranes and/or electrodes employed therein. Without being limited to a particular mechanism of action, the methods creating an IDZ, including after extended exposure of the nanoporous membrane to blood plasma, protect the membrane from biofouling by preventing contact of the membrane with high concentrations of biomolecules (e.g., proteins) found in plasma. In an aspect, the IDZ protects the membrane from biofouling after contact with blood plasma for at least 10 hours, or at least 12 hours. Again, without being limited to a particular mechanism of action, the use of fluorescent dyes to track the neutral stream (i.e. the dialysate) shows that some neutral compounds are excluded from the IDZ due to intermolecular interactions with charged species, which further reduces the risk of biofouling of the membranes.

The methods of ICP to separate two streams within the branched microchannel of the device provides a first stream of fluid from the blood plasma to source as a subject (or patient)-derived dialysate, and thereafter using the dialysate to accept metabolic waste during hemodialysis. Beneficially, the first stream of the neutral waste can be circulated to an auxiliary channel that contacts the 'exit' (opposite end) of the ion selective membrane. Such neutral waste can accept ions (e.g. Na$^+$ or K$^+$) that are transported across the membrane to sweep away the excess salt and continuously renew the membrane's ability to transport salt out of the blood plasma. This stream and the remaining neutral waste can then continue to a collection device for removal or be routed to further use as a dialysate. The second stream provided contains the proteins and other charged components of the blood plasma, which can be recombined with the subject (or patient's) blood and undergo hemodialysis.

Generally, as referred to herein the hemodialysis step includes the use of a hemodialysis membrane, which is a semipermeable membrane having microscopic holes that permit limited substances to cross the membrane (e.g., a molecular weight cutoff filter). The semipermeable membrane allows water and waste to pass through, but does not allow blood cells and large proteins to pass through. In some embodiments, the hemodialysis membrane is comprised of a biocompatible material about 100 nm to about 1.0 mm thick traversed by pores with a monodisperse or polydisperse distribution of diameters such that species having a molecular weight below about 3,000 Da, about 10,000 Da, about 30,000 Da, or about 60,000 Da are permitted through. The purpose of dialysate which has been at least partially generated by the methods described herein from the patient's blood plasma, is to accept toxins from the blood that have passed through the semipermeable membrane.

The methods and devices of the invention overcome the conventional limitations of a dialysis step, namely the limitations of employing hemodialyzers requiring large volumes of dialysate. Beneficially, the methods allow use of a hemodialysis membrane without such limitations. Hemodialyzers remove metabolic waste by ultrafiltration, employing hydrostatic pressure to overcome osmosis, and a filter for size-selective retention of essential blood components (e.g., blood cells and albumin). In an embodiment, electromigration can be employed with a hemodialysis membrane to enhance waste clearance. In an embodiment, a step of inducing electromigration of charged species across dialysis membranes located to either side of the plasma stream is employed. Beneficially, the incorporation of electromigratory transport into hemodialysis can lead to an enhancement in transport—including difficult-to-remove 'middle molecules' (MW 500 to 60,000 Da). In an embodiment, a reduced membrane thickness along with application of an increase in transmembrane flux, such as about 10 mV increased transmembrane flux, can increase results of the hemodialysis membrane.

In a preferred embodiment, the methods do not require an additional (or external) source of dialysate. In other embodiments, the methods significantly reduce the volumetric requirement for additional (or external) source of dialysate, in an aspect by at least 50%, at least 55%, at least 60%, at least 65%, at least 70%, at least 75%, at least 80%, at least 85%, at least 90%, or at least 95%.

In an embodiment, the input to a hemodialysis unit (or hemodialysis membrane) is the patient's blood (less a fraction of excess fluid) and the dialysate produced according to the methods of the invention. To conserve this fluid, the methods beneficially reduce the rate of consumption of dialysate to more closely match the rate at which fluid is excreted by normally functioning human kidneys. To achieve this reduced rate of dialysate consumption, the flux of metabolic waste across the hemodialysis membrane should be enhanced. The methods of the invention initiate both convection (by electroosmosis) and electromigration across the membrane, neither of which modes of transport contain a concentration gradient term, but are instead dependent upon the absolute concentration of species available for transport. Therefore, they are capable of operating against concentration gradients, and therefore, it becomes possible that the concentration of waste in the dialysate can exceed that extent in the blood.

When a transmembrane potential is applied, the surface properties and range of pore sizes in the membrane filter will greatly influence the direction and magnitude of electroosmosis and will determine whether cations or anions are permitted. As a matrix, blood is highly complex and host to solutes with a wide range of electrophoretic mobilities ('charge-to-drag ratios'). The depletion of more mobile solutes is favored by the system with the addition of an electric field.

Devices

The incorporation of the ICP process and methods as generally disclosed herein allow for an approach to kidney disease management that avoids a dialysate reservoir. The removal of the reservoir greatly reduces the size of the dialysis system, allowing the system to be confined to a wearable device to provide for greater flexibility for the user of the device, while still providing the necessary health benefits. Such a wearable device can utilize the electrokinetic methods as disclosed herein to separate waste products from the blood. Further, while the term "wearable device" is used herein, it should be appreciated that the device and/or any aspect or embodiment thereof, may be implanted in a patient to provide for the continuous or near-continuous cleansing of the blood supply. Thus, the device can be a form of an implantable filter.

Figure 7:
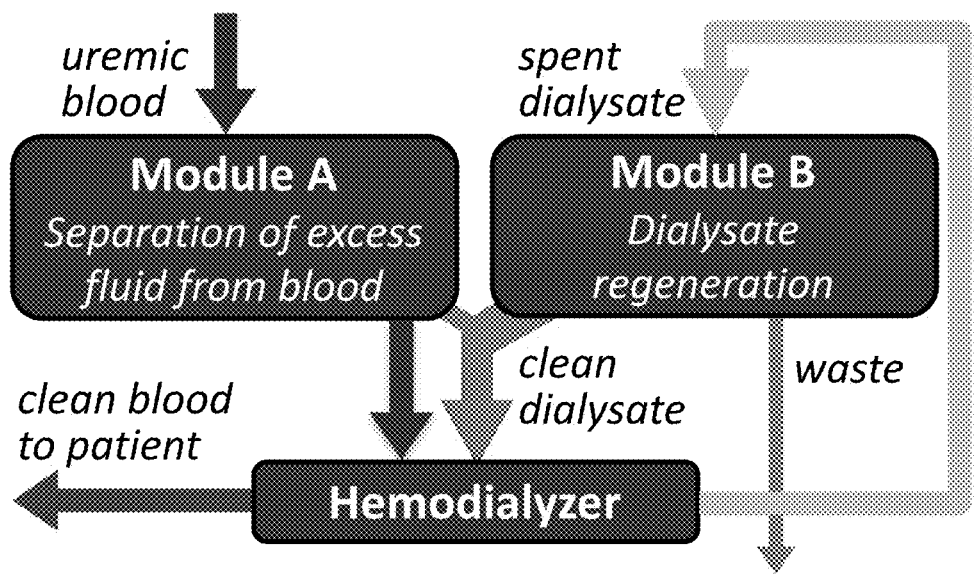
FIG. 7 shows an embodiment of a modular microfluid device according to embodiments of the invention.

The device can be a modular device microfluidic device, such as depicted in FIG. 7 that obviates the need for a dialysate reservoir by using electrokinetic means to generate dialysate from the excess fluid in the patient's bloodstream. As depicted in FIG. 7, Module A continuously separates excess fluid from blood which can beneficially thereafter be combined with concentrated additives to yield clinical grade dialysate. The resulting fluid will be employed as an in-line source of dialysate by the hemodialyzer. Module B will regenerate dialysate (by ICP-based separation) after it is spent. The purified dialysate generated by Modules A and B will be supplied to a hemodialyzer that employs the patient-derived dialysate to accept charged metabolic waste components from the plasma through a molecular weight cutoff (MWCO) filter (such as between 15 kDa and 65 kDa). This hemodialyzer can also induce electromigration of charged waste products across the dialysis membrane, thereby increasing the efficiency of waste removal and reducing dialysate consumption. These individual technologies work in concert, to accomplish hemodialysis without an external source of dialysate. The device can be microfluidic and take the form of a microfluidic junction, which is shown generally in the exemplary figures. The device therefore comprises channels to direct the flow of the blood/plasma. The channels can also be referred to as branches of the device. The ratio of the cross-sectional branches or channels can vary by design of the device. In an embodiment, the ratio of branches is about 1:1. However, in other embodiments, the ratio of branches is about 1:2, about 1:3, about 1:4, about 1:5, about 1:6, about 1:7, about 1:8, about 1:9, or greater. In certain embodiments, having unequal ratios of the branches is desired to enhance the enrichment of surfactants that can be employed to assist in further separation of neutral compounds from one of the streams of the device. In such an embodiment where a surfactant is employed in the methods of the invention, it is desirable to have a narrow channel where the surfactant is deflected to decrease costs as a design consideration to reduce the amount of surfactant required for a local concentration that approaches, meets or exceeds a critical micelle concentration (CMC) as described herein.

The channels can comprise glass and/or polydimethylsiloxane (PDMS). PDMS belongs to a group of polymeric organosilicon compounds that are commonly referred to as silicones. The PDMS/glass devices may be fabricated using standard soft lithography. While the devices employed in the examples here are PDMS/glass, the channels can comprise any biocompatible material (e.g., polyvinylchloride, polypropylene, polysulfone, polyethylene, etc.) that can be fashioned (e.g., by molding, embossing, laser cutting or 3D printing) into channel structures.

According to some aspects, the device comprises a microfluidic device that includes an inlet channel terminating at a junction. The junction includes a first branch and a second branch extending therefrom. The plasma can flow through the inlet. A charged membrane, and will be disclosed herein, can be positioned at or near the junction, wherein the charged membrane will aid in separating the charged particles and charged molecules from the blood. Such a membrane can comprise Nafion or any of the other membranes disclosed and/or referenced herein and/or incorporated by reference. Thus, the first branch will include charged species and some of the uncharged (neutral) components of the plasma, while the second channel will include substantially neutral plasma components. The plasmas will be recombined, such as at a second junction, into a treatment channel. The treatment channel can also comprise PDMS, glass, silicon, or a biocompatible polymeric material. The charged particle/plasma combination will be generally centrally positioned in the treatment channel with the fluid comprised substantially of neutral plasma components annularly surrounding, or in planes above and below. A hemodialysis membrane can be used to separate the streams and to allow for dialysis to occur, with the fluid containing neutral plasma components constituting the dialysate.

It is envisioned that the treatment channel utilizes the substantially neutral plasma fluid to serve as dialysate for on-chip hemodialysis, which removes the need for an outside source of dialysate, which allows for the smaller size of the device and for more comfortable use thereof.

As disclosed herein, the method, device, and/or system according to the aspects will include the use of a membrane to deplete excess salt. The membrane may be referred to generally as an ion selective membrane. According to aspects of the disclosure, the process within the device can be tweaked or otherwise set up to tune the properties of the ion selective membrane to deplete salts selectively. This can include adding a coating or coatings to the membrane.

For example, as included herein, it is envisioned that the membrane comprises Nafion. It has been demonstrated that certain polyelectrolyte coatings increase the selectivity of Nafion for monovalent (e.g. $Na^+$, $K^+$) over divalent (e.g. $Mg^{2+}$, $Ca^{2+}$) cations. Further, materials containing binding pockets, such as crown ethers, have high innate selectivity for cations, such as that of 15-crown-5 for sodium. Still further, and according to some aspects of embodiments, the device includes an ion selective structure from a bed of polymer-coated nanobeads. Such nanobeads have been shown to include an ion depletion capability due to their high conductivity and highly charged surface coatings. The bead beds are highly versatile in that their porosity, ionic conductivity, and selectivity have the potential to be tuned over a very wide range. For example, two types of beads, each with unique coatings could be combined to fine tune the selectivity for $Na^+$ and $K^+$.

Therefore, it is to be appreciated that the device includes a membrane material or combination of materials that yields the best blood composition. Such a membrane can comprise a base of generally any ion selective material, such as, but not limited to Nafion, Aciplex, Selemion, FAS, FKS, Ralex, PC-SK, PC-SA, Morgane, Neosepta, TWEDG, TWCED, in addition to other anion and cation exchange membranes, such as those disclosed by Tongwen Xu in the Journal of Membrane Science 263 (2005) 1-29, which is herein incorporated by reference in its entirety. Ion-exchange membranes are made of a polymeric material attached to charged ion groups. Anion-exchange membranes contain fixed cationic groups with predominantly mobile anions; because anions are the majority species, most of the conductivity is due to anion transport. Cation-exchange membranes contain fixed anionic groups with predominantly mobile cations; because cations are the majority species, most of the conductivity is due to cation transport. There are two primary classes of membranes: heterogeneous and homogeneous. Heterogeneous membranes have low cost and a thicker composition with higher resistance and a rough surface that can be subject to fouling. Homogeneous membranes are more expensive, but have a thinner composition with lower resistance and a smooth surface, less susceptible to fouling. Homogeneous membrane surfaces can be modified to alter the membrane permselectivity to protons, monovalent ions, and divalent ions.

Additionally, the wearable device can include in-line quality control features, such as sensors. According to aspects of the invention, electrochemical sensors can be incorporated into the device to monitor the levels of selected blood components. Of particular interest to diabetic patients is an integrated glucose sensor. Such a glucose sensor can comprise enzyme-based or enzyme-free type sensors that is incorporated into the device. The sensor can be electronically coupled, such as via a transmitter, to a monitor on the device or transmitted wireless to an external device to provide continuous updates on the glucose levels. Such wireless communication can utilize Wi-Fi, Bluetooth, near-field technology, air play technology, or generally any additional technology capable of transmitting readings from the sensor to a user display, such as a graphical user interface or non-graphical user interface. Further, blood urea nitrogen (BUN) can be monitored in the blood before and after purification as a real-time indicator of patient status and device performance. Such a BUN sensor can also be incorporated in a manner similar to that of the glucose sensor to provide for real-time display of the BUN levels, and can be wired or wirelessly transmitted to a display or interface of the device, or otherwise transmitted to the cloud or other database (tablet, phone, computer, server, cloud, or any other device including a processor, such as a CPU). Such a database can store the data for historical review and for providing any adjustments to the materials, treatments, or anything else associated with the device. Therefore, the wearable device can incorporate such sensors to monitor the blood as it travels through the wearable device.

Additionally, the wearable device can include intelligent control and communication components. Examples of such intelligent control units may be tablets, telephones, handheld devices, laptops, user displays, or generally any other computing device capable of allowing input, providing options, and showing output of electronic functions. Still further examples include a microprocessor, a microcontroller, or another suitable programmable device) and a memory. The controller also can include other components and can be implemented partially or entirely on a semiconductor (e.g., a field-programmable gate array ("FPGA")) chip, such as a chip developed through a register transfer level ("RTL") design process. The memory includes, in some embodiments, a program storage area and a data storage area. The program storage area and the data storage area can include combinations of different types of memory, such as read-only memory ("ROM"), random access memory ("RAM") (e.g., dynamic RAM ("DRAM"), synchronous DRAM ("SDRAM"), etc.), electrically erasable programmable read-only memory ("EEPROM"), flash memory, a hard disk, an SD card, or other suitable magnetic, optical, physical, or electronic memory devices.

Additionally, the wearable device can include a communications module and can be configured to connect to and communicate with another controller, such as a computer, tablet, server, or other computing device. This could allow the device to provide data or other information (e.g., warnings, status, notices, etc.) associated with the device to a remote location of the additional controller to allow the real-time information and stored information for the device. The information could be used to determine issues, forecast, or otherwise track information related to the device. The communication could also be in the form of inputs such that the communication could include a command to the device from a remote location.

In some embodiments, the device can include a first communications module for communicating with a secondary device (other device or remote controller), and/or a second communications module for communicating with a central location (server, computer, or other master controller). For sake of simplicity, the term "communications module" herein applies to one or more communications modules individually or collectively operable to communicate with both the mobile reader and the central location. In an aspect, the communications module communicates with the central location through the network. In some embodiments, the network is, by way of example only, a wide area network ("WAN") (e.g., a global positioning system ("GPS"), a TCP/IP based network, a cellular network, such as, for example, a Global System for Mobile Communications ("GSM") network, a General Packet Radio Service ("GPRS") network, a Code Division Multiple Access ("CDMA") network, an Evolution-Data Optimized ("EV-DO") network, an Enhanced Data Rates for GSM Evolution ("EDGE") network, a 3GSM network, a 4GSM network, a Digital Enhanced Cordless Telecommunications ("DECT") network, a Digital AMPS ("IS-136/TDMA") network, or an Integrated Digital Enhanced Network ("iDEN") network, etc.), although other network types are possible and contemplated herein. In certain embodiments, the network is a GSM or other WAM which is operable to allow communication between the communications module and the central location during moments of low-quality connections. The network can be a local area network ("LAN"), a neighborhood area network ("NAN"), a home area network ("HAN"), or personal area network ("PAN") employing any of a variety of communications protocols, such as Wi-Fi, Bluetooth, ZigBee, near field communication ("NFC"), etc., although other types of networks are possible and are contemplated herein. Communications through the network by the communications module or the controller can be protected using one or more encryption techniques, such as those techniques provided in the IEEE 802.1 standard for port-based network security, pre-shared key, Extensible Authentication Protocol ("EAP"), Wired Equivalency Privacy ("WEP"), Temporal Key Integrity Protocol ("TKIP"), Wi-Fi Protected Access ("WPA"), and the like.

In an embodiment, connections between the communications module and the network are wireless to enable freedom of movement and operation of the mobile device without being physically tethered to a computer or other external processing device to facilitate such communications. Although such a modality of communications is preferred for at least this reason, it is contemplated that the connections between the communications module and the network can instead be a wired connection (e.g., a docking station for the communications module, a communications cable releasably connecting the communications module and a computer or other external processing device, or other communications interface hardware), or a combination of wireless and wired connections. Similarly, the connections between the controller and the network or the network communications module are wired connections, wireless connections, or a combination of wireless and wired connections in any of the forms just described. In some embodiments, the controller or communications module includes one or more communications ports (e.g., Ethernet, serial advanced technology attachment ("SATA"), universal serial bus ("USB"), integrated drive electronics ("IDE"), etc.) for transferring, receiving, or storing data.

In an embodiment, the communications module can be powered by a dedicated power source, such as a battery, battery pack, or wired power (e.g., AC power socket or other power source). In some aspects of the invention, the communications module can be powered by the same power supply as that of the dispenser, such as by battery or by wired power. Still further, it is contemplated that the communications module can be powered wirelessly or by power over ethernet. The central location can include a centrally located computer, a network of computers, or one or more centrally located servers. The central location can be adapted to store, interpret, and communicate data from the device, and can also interpret the data and communicate the interpreted data to a user.

Therefore, the device can be wearable and inclusive in nature. In addition, the device may be implantable such that the components, or at least some components are internal to a patient. The removal of the dialysate reservoir greatly reduces the size and number of components required. The microfluidic chambers allow for the continuous blood flow through the device in a slower and controlled manner. The incorporation of sensors, battery, communication systems, and/or displays or interfaces can also be incorporated on a level that will not increase the size of the device. Such components can be on the device itself or on another device, such as another wearable (e.g., smart watch, necklace, etc.) or transmitted to a device that includes such a display (e.g., phone, tablet, etc.) The membrane material can be selected based upon information obtained from the user and/or continued research to best "tune" the material to be selective, as disclosed herein.

Figure 20:
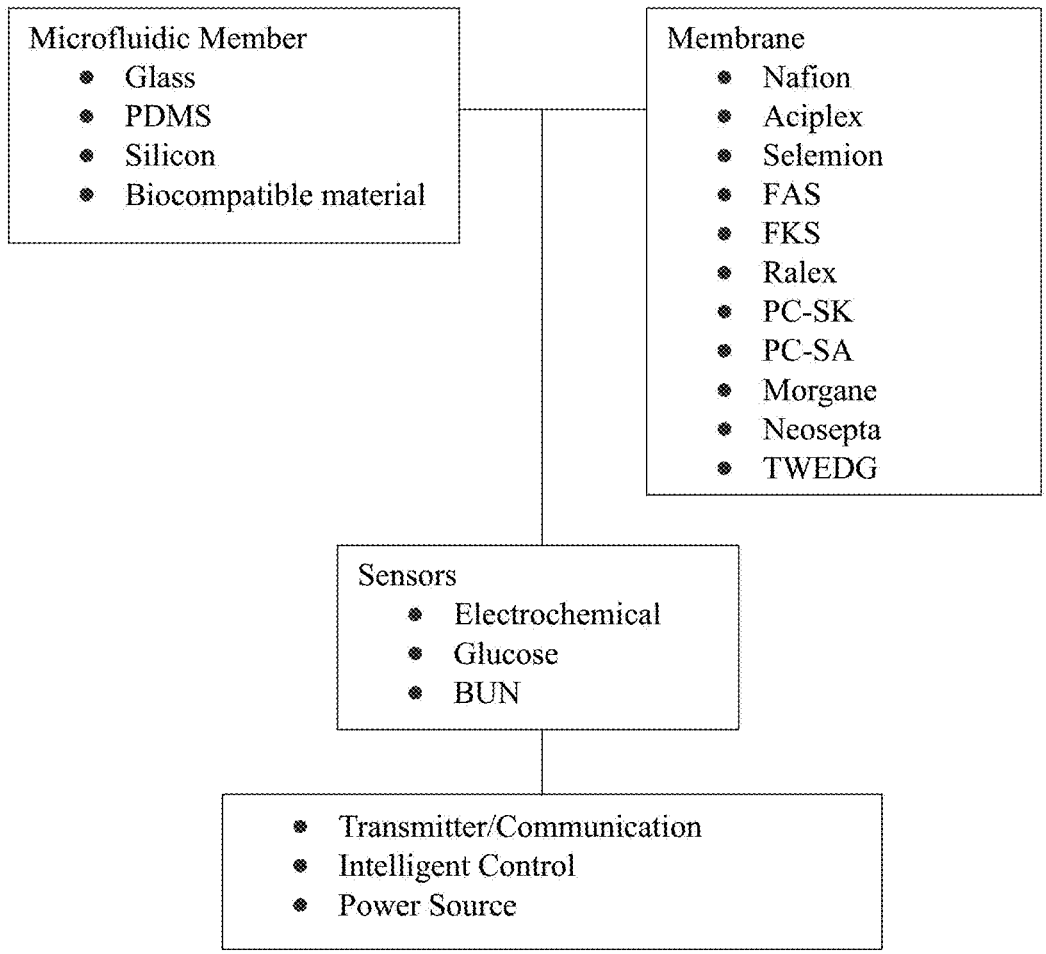
FIG. 20 is a schematic representation of components of a wearable device according to aspects of the invention.

Such a representative device with components is shown generally in the schematic of FIG. 20, wherein the device comprises the microfluidic member and associated membrane. Additionally, in some embodiments the sensors can be associated with the wearable device, and can include one or more sensors as disclosed herein. Additional components, such as including, but not limited to, transmitters and/or communication members, intelligent control (processors, chips, circuit boards, etc.), and power sources can be included to make the device as convenient and useful as possible for wearing and operating as disclosed herein. However, it should be appreciated that the figure and relative disclosure as included herein is not to be considered limiting, and that additional components may be included and/or components may not be needed in all embodiments in order to provide a working wearable device as disclosed.

Methods of Treating Kidney Disease, Providing Hemodialysis and/or Mitigating Edema In an embodiment, a method for treating kidney disease is provided. In a further embodiment, a method for hemodialysis is provided. Various indications for hemodialysis and the need to treat kidney disease include, for example, end-stage renal disease (ESRD) including due to diabetes, hypertension, certain autoimmune conditions, and other kidney diseases. The methods of use are particularly well-suited for the treatment of kidney disease, including patents awaiting transplants and requiring frequent dialysis.

In a still further embodiment, a method for mitigating edema is provided, including the reduction of excess fluid and urea. In a still further embodiment, a method for continuously removing excess fluid from blood plasma and repurposing it as dialysate is provided. The methods are further useful for alleviated, mitigating and/or controlling the discomfort and physical strain associated with edema, including peripheral edema which can cause weight gain, edema, shortness of breath, and rapid pulse. Still further the methods are suitable for the removal of waste build-up in a patient with the need for dialysis and/or having insufficient access to dialysis. Still further, the methods are particularly well-suited for treatment including reduction of excess fluid built up between dialysis sessions.

Beneficially, the methods described herein provide a subject or patient in need thereof with the ability to undergo hemodialysis without the physical constraints and size limitations associated with a traditional hemodialyzers and other portable machines required for the filtering of blood. Due to the removal of a dialysate reservoir and sheath fluids, the methods described herein enable a miniaturized hemodialysis device that provides the beneficially effects of removing wastes (e.g. salts and urea) from the blood plasma while retaining protein content thereof.

In an aspect, the methods are applied to blood plasma of a subject in a continuous fashion, such as about 0.01-50 mL/minute, or about 10-50 mL/minute of a dialysate of a subject or patient in need thereof. Beneficially, such a continuous fashion would provide equivalent volume of dialysate in a conventional intermittent hemodialysis treatment of a patient during an average 3-hour session at a medical center. In another aspect, a method that removes excess fluid from blood plasma and repurposing it as dialysate can be combined with an in-line dialysate regeneration. In any aspect, the repurposing of excess blood plasma volume as dialysate according to the methods described herein significantly reduces the rate of consumption of in-line dialysate.

In an aspect, the methods are applied to blood plasma—and not whole blood. In an aspect, the blood plasma can be separated from whole blood by various known techniques, including for example dielectrophoresis. An exemplary and non-limiting example of dielectrophoresis is shown in FIG. 2. The use of blood plasma ensures that the use of methods, namely ICP, does not damage blood cells. However, without being limited to a particular mechanism of action, the methods can be applied to a plasma source of a subject or patient that can be continuously skimmed from whole blood and supplied to the ICP.

In an aspect, each of the methods comprise, consist of and/or consist essentially of removing neutral compounds from blood plasma of a subject or patient in need thereof by ion concentration polarization, obtaining fluid from the blood plasma to source as a subject (or patient)-derived dialysate, and thereafter using the dialysate to accept metabolic waste during hemodialysis. As referred to herein, the removal of neutral compounds (e.g. water and small neutral molecules) from blood plasma by ion concentration polarization (ICP) refers to the simultaneous enrichment and depletion of ions at opposing ends of an ion permselective membrane or bipolar electrode when an electrical voltage is applied across it.

In a further aspect, each of the methods comprise, consist of and/or consist essentially of providing a subject in need of hemodialysis with a branched, flow-through microfluidic device as described herein, applying a charge to the device, and thereafter providing to the device plasma from a subject or patient in need thereof. The methods may further comprise, consist of and/or consist essentially of separating neutral compounds from charged compounds in the blood plasma to remove neutral compounds by ion concentration polarization, generating a fluid dialysate from the blood plasma, and thereafter contacting the dialysate with a hemodialysis membrane to accept metabolic waste from the subject in need thereof.

In an aspect, the methods of separating the neutral stream from the charged stream can utilize a voltage and/or ion selective membrane. Ion selectivity may also be referred to as an ion permselective membrane. These membranes are comprised of highly charged nanopores or nanochannels that electrostatically exclude co-ions. For example, the material Nafion contains nanochannels lined with negatively charged sulfonate groups and thereby excludes anions. Nafion is an exemplary membrane and one skilled in the art will appreciate other membranes suitable for use in the methods and device described herein.

When a voltage is applied across such a membrane, cations are selectively transported through it while anions will migrate towards the anodic driving electrode, resulting in an ion depletion zone (IDZ) in the anodic compartment. The low ionic conductivity of the IDZ leads to a strong (>10 fold) local enhancement of the electric field and the formation of concentration and electric field gradients the IDZ boundary. The membrane favors depletion of monatomic ions (over molecular cations) due to their small size and high electrophoretic mobility. Significantly, the properties of the membrane can be further tuned to selectively deplete Na+ or K+, a clinically favorable process. Meanwhile, high-mobility anions (e.g. HCO3- or Cl—) will migrate out of the IDZ toward the anodic driving electrode and are therefore also locally depleted.

In an aspect, the methods can further include a step of adding a surfactant to the inlet of the device to enhance the separation and removal of neutral species. Beneficially the use of surfactants to form micelles to remove neutral compounds from the dialysate replaces the need for using a sorbent to pull out the neutral compounds. Any ionic surfactant can be used to enhance separation and removal of neutral species as the micelles formed bind to neutral species. Exemplary surfactants include anionic, cationic and zwitterionic surfactants.

Anionic surfactants have a negative charge on the hydrophobe; or surfactants in which the hydrophobic section of the molecule carries no charge unless the pH is elevated to neutrality or above (e.g. carboxylic acids). Carboxylate, sulfonate, sulfate and phosphate are polar (hydrophilic) solubilizing groups commonly found in anionic surfactants. Accordingly, examples of anionic surfactant groups include sulfonic acid salts, alcohol sulfates, alkylbenzene sulfonates, phosphoric acid esters, and carboxylic acid salts.

Cationic surfactants are classified as cationic if the charge on the hydrotrope portion of the molecule is positive. Surfactants in which the hydrotrope carries no charge unless the pH is lowered close to neutrality or lower, but which are then cationic (e.g. alkyl amines), are also included in this group. The cationic surfactant field is dominated by nitrogen containing compounds, probably because synthetic routes to nitrogenous cationics are simple and straightforward and give high yields of product, which can make them less expensive. Cationic surfactants preferably include, more preferably refer to, compounds containing at least one long carbon chain hydrophobic group and at least one positively charged nitrogen.

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds.

Adding an ionic surfactant that is above the critical micelle concentration (CMC) enhances neutral compound separation. A skilled artisan will ascertain from literature sources the CMC of a surfactant and methods for measuring the same. The surfactant can be dosed to at the inlet of the device to meet or exceed the CMC of the utilized surfactant. Reaching the CMC of the surfactants ensures formation of micelles to bind the neutral species to enhance removal. As one skilled in the art will ascertain, the CMC of the surfactant will differ according to the device structure employed. A lower concentration of surfactant will be required when a device having smaller channels for the neutral species is employed. This beneficially provides the need for reduced surfactant concentration to meet and exceed the CMC when dosed locally to the channel as opposed to a concentration dosed at the input of the device. When the surfactant and neutral compounds are deflected (i.e. surfactant cannot cross the membrane of the device) into a narrower channel the surfactant is enriched and a lower concentration is required.

In an aspect, the methods can further include a step of contacting the neutral stream (i.e. dialysate) with a purification media and/or incorporating hemodialysis additives. In an embodiment, the dialysate is purified by flowing through a sorbent bed as the purification media to yield purified water before optionally incorporating hemodialysis additives. Exemplary sorbent bed materials include for example, on-chip sorbents for processing neutral waste including micro- or nano-particulate media such as silica or activated carbon. In a further aspect, hemodialysis additives can include, for example, a bicarbonate source.

In an aspect, the methods do not damage essential blood components, such as proteins. In a further aspect, the methods beneficially do not lose protein content from the plasma, including albumin, into the neutral stream of branch of the device with the use of the ICP. In an aspect, the methods do not cause hypoalbuminemia. In an aspect, at least about 90%, at least about 91%, at least about 92%, at least about 93%, at least about 94%, µ at least about 95%, at least about 96%, at least about 97%, at least about 98%, or preferably at least about 99% of the protein including albumin content of the plasma source is retained in the charged stream (or the second stream of the method) and not lost to the neutral stream (or the first stream) which becomes the dialysate.

In an aspect, the methods do not result in biofouling of the membranes and/or electrodes employed therein.

In an embodiment, a single micro-/nano-junction can be scaled to accommodate ICP-based separation at a flow rate of about 1.0 nL/min to about 100 µL/min. Beneficially, these junctions can be operated in parallel (multiplexed) to provide the flow rate required for the proposed application as determined by the supply rate of dialysate required for continuous hemodialysis.

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications to the embodiments of the invention to adapt it to various usages and conditions.

EXAMPLES

Example 1

Materials.

Texas Red dye-labeled albumin and the neutral (uncharged) fluorophore BODIPY FL (4,4-difluoro-4-bora-3a, 4a-diaza-s-indacene) were obtained from Molecular Probes (Eugene, Oreg.). Human blood plasma sample (K2EDTA) was purchased from Discovery Life Sciences (Los Osos, Calif.), divided into 100 µL aliquots, stored frozen at 80° C., and thawed at 37° C. before use. All other solutions were made with reagent grade chemicals (Fisher Scientific, Waltham, Mass.) and diluted with double deionized water (18.2 MΩ·cm, Sartorius Arium Pro, Göttingen, Germany) before use to desired concentration. A solution which modeled the ionic strength and pH of blood consisted of a solution of 50.0 mM NaCl and 5.0 mM KCl in 20.0 mM carbonate buffer adjusted to pH 7.45 with 0.1 M HCl. Poly(dimethylsiloxane) (Sylgard 184 elastomer kit, Dow Corning Corp., Midland, Mich.) was used for device fabrication. Platinum electrodes (99.95%) were purchased from Strem Chemicals (Newburyport, Md.). A 3.0 µM solution of Pluronic F-108 (Poly(ethylene glycol)-block-poly(propylene glycol)-block-poly(ethylene glycol)) (Millipore Sigma, St. Louis, Mo.) in 10.0 mM phosphate buffer (pH 7.2) was used to coat the microchannels. Nafion perfluorinated resin (20 wt % solution in lower aliphatic alcohols) was purchased from Sigma Aldrich (St. Louis, Mo.) and used as received.

Device Fabrication.

The PDMS/glass devices were fabricated using standard soft lithography. The main (branched) microfluidic channel was 48.0 µm tall and 10.0 mm long having a 500 µm wide inlet segment leading into two 250 µm wide branches at a location 5.0 mm from the inlet. A 4.0 mm diameter biopsy punch was used to create the inlet and outlet reservoirs. Near the branching junction, at a location indicated as in the Results and Discussion section, a mechanical incision was made using a scalpel blade and subsequently filled with 5.0 µL of Nafion. The Nafion was then cured at 95° C. for 10 min. Excess Nafion was removed by repeating applying and peeling away low residue tape. The PDMS layer and glass slide were treated in an air plasma (PDC-001, Harrick Plasma, Ithaca, N.Y.) for 90 seconds and then bonded together. Immediately after bonding, all microfluidic devices were rinsed with deionized water and coated by filling with Pluronic solution and incubating at 4.0° C. for at least 18 h.

Ion Concentration Polarization.

Prior to ICP experiments, each device was rinsed with 10.0 mM phosphate buffer solution for 30 min to remove excess Pluronic. The rinsing solution was then replaced with the sample solution. A driving voltage was applied across the nanojunction using a DC power supply (HY3005D, Mastech and DIGI360, Electro Industries, Westbury, N.Y.) connected to Pt electrode wires positioned in the reservoirs. The volume of solution and voltages employed at each reservoir for individual experiments are indicated in the Results and Discussion section.

Fluorescence Measurements.

All fluorescence measurements were performed using an Eclipse Ti-S inverted fluorescence microscope (Nikon Industries, New York, N.Y.) equipped with a digital camera (Orca-4.0, Hamamatsu Corp., Bridgewater, N.J.). All images were processed using NIS-Elements 4.6 software (Nikon). Fluorescence measurements used for quantitative comparison of species concentrations were background subtracted.

Fluorescence microscopy was employed to characterize the behavior of charged and neutral compounds in ICP-based separations. The first separation was carried out in a solution of model blood (matched salinity and pH) and the second in undiluted blood plasma. The device was then adapted to prevent damage to proteins and to reduce operating voltage. Finally, factors impacting device lifetime were evaluated and determined the composition of the neutral stream.

ICP-Based Separation of Albumin from a Neutral Dye in Model Blood.

Figures 3A, 3B:
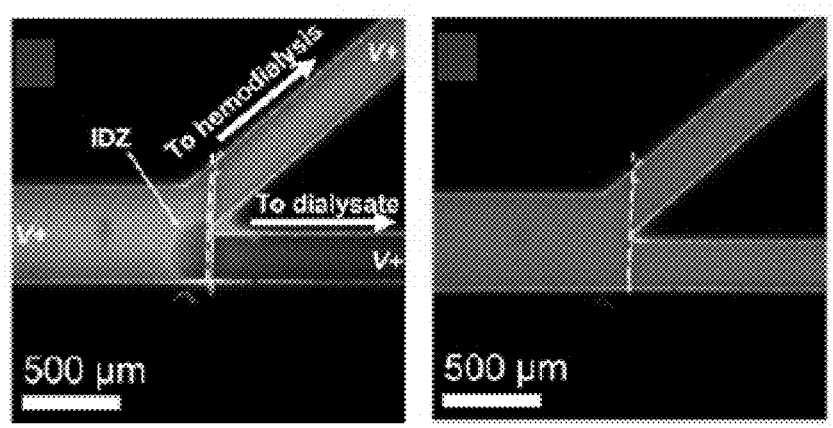
FIGS. 3A-3B show fluorescence micrographs of the location of dye-linked albumin and BODIPY FL (representative both of the charged species and neutral species present in model blood plasma).

FIG. 3A shows the separation of albumin (labeled with Texas Red) from an uncharged dye (green, BODIPY FL) at an ion permselective junction (white dashed line) in a solution that models the pH and salinity of blood. The solution contained 0.05 mg/mL dye-linked albumin (approx. 1.0% of the concentration of albumin in human blood) and 1.0 µM BODIPY in 50.0 mM NaCl, 5.0 mM KCl, and 20.0 mM carbonate at pH 7.45. In this experiment, first the main channel was rinsed with the sample solution for 2 min. Second, the volume of sample solution in the reservoirs was adjusted to 40.0 µL (inlet) and 15.0 µL (both outlets) to generate flow from left to right (as in Scheme 1a of FIG. 1). Finally, 40.0 V was applied at all three reservoirs of the main channel versus the auxiliary channel (ground). The IDZ formed immediately upon application of the driving voltage (FIG. 3A). After the voltage was turned off, the IDZ dissipated, and the albumin and uncharged dye uniformly filled the main channel (FIG. 3B). In the evaluated embodiment, the driving voltage is applied in the inlet and both outlets of this branched microchannel (labelled as V+), a configuration traditionally employed for desalination.

ICP-Based Separation in Blood Plasma.

Figure 4:
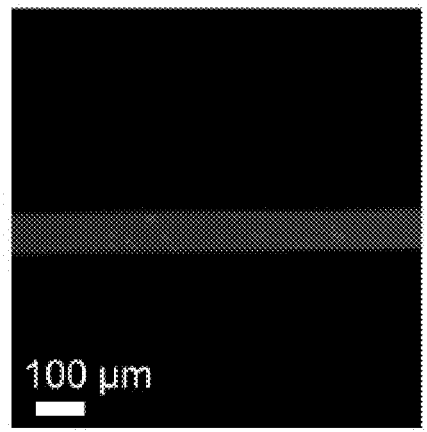
FIG. 4 shows fluorescence micrograph showing the appearance of protein aggregates (bright spots) in blood plasma in the inlet segment after the application of 40.0 V for 1 min and then 24.0 V for 10 min.

When this three-driving-electrode configuration was used to perform a similar separation in blood plasma, protein aggregates were observed in the inlet segment of the main channel (FIG. 4). These results were obtained in a device with smaller dimensions (5 times narrower channels and 19.5 µm channel height) than was used in the other experiment. In this experiment, the channel was first rinsed with 10.0 mM phosphate buffer, and the buffer in the inlet reservoir was replaced with 40.0 µL of 0.05 mg/mL dye-linked albumin in blood plasma. Then, the volume in the outlet reservoirs was adjusted to 14.0 µL to generate pressure driven flow of the plasma through the main channel. Finally, a driving voltage of 40.0 V was applied, as in the prior experiment, and was subsequently decreased to 24.0 V. FIG. 4 was obtained approximately 10 min after the driving voltage was applied. Bright spots were observed in the inlet segment of the main channel and attributed to the formation of aggregates of the dye-linked albumin. Without being limited to a particular mechanism of action, such aggregates are likely due to interaction of blood components with the products of Faradaic reactions at the driving electrode located in the inlet. During this experiment, it was also observed that having the Nafion-filled cut positioned across the full width of the main channel often led to the formation of a large IDZ, which blocked entrance of charged species to both branches.

Development of an Enhanced Scheme for Separation in Blood Plasma.

To address the formation of protein aggregates, an alternative one-electrode scheme was developed, which prevents contact of the blood plasma with driving electrodes. In this scheme, the single electrode was located in the outlet of the neutral stream, while the inlet and remaining outlet were at a floating potential. This adaptation is important because contact between blood plasma and electrodes is completely avoided, which is desirable to ensure integrity of the blood that is returned to the patient. To avoid blocking both branches with the IDZ, the permselective membrane was relocated to a position past the branching junction into the neutral stream. Using this strategy, the IDZ was more readily contained in the lower branch, which increased tolerance for variations in inflow rates. Further, a double ion-selective junction (As shown in Scheme 1b of FIG. 1, and white dashed lines, FIG. 5) was employed to increase the rate of ion depletion and the length of the neutral stream branch was shortened from 5.0 mm to 2.5 mm. In combination, these changes reduced the required driving voltage from 40.0 V to 12.0 V while still creating a sufficient IDZ volume to fill the entire cross section of the entrance to the neutral stream. Significantly, this approach resulted in as high as 99.7% retention of albumin and successful separation of neutral metabolites and excess fluid to be utilized as precursor to dialysate.

Figure 5:
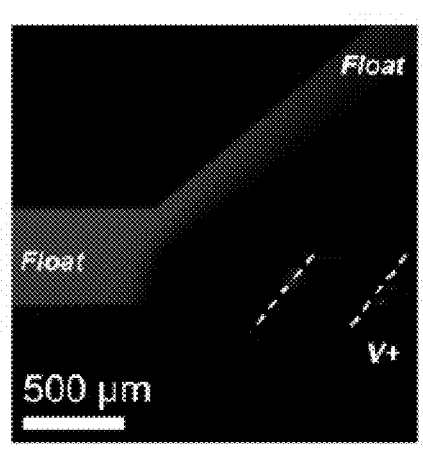
FIG. 5 shows fluorescence micrograph showing the location of dye-linked albumin in undiluted blood plasma, where the dye-linked albumin is redirected into the upper branched channel under an applied voltage of 12.0 V.

FIG. 5 shows the repulsion of dye-linked albumin from the boundary of an IDZ in undiluted blood plasma. The experiment proceeded as follows. First, the channel was rinsed with 10.0 mM phosphate buffer, after which the buffer in the inlet reservoir was replaced with 40.0 µL of 0.05 mg/mL dye-linked albumin in model blood. The volume in the outlets was adjusted to 20.0 µL to establish fluid flow. Second, a driving voltage of 24.0 V was applied. This initial step allowed the formation of the IDZ to be observed—indicating proper function of the device—before the addition of blood plasma. After 5 min, the sample solution in the inlet was replaced with 40.0 µL of 0.05 mg/mL dye-linked albumin in undiluted blood plasma. Third, the flow rate and voltage were adjusted to adjust the position of the IDZ boundary to the branching junction. Specifically, the inlet volume was adjusted to 33.0 µL and the outlets to 12.0 µL, and the driving voltage decreased to 12.0 V. The change in fluorescence intensity measured in the neutral stream (dashed line, FIG. 5) 10 min after the voltage was applied, indicates exclusion of albumin from this branch. This result is significant because albumin, an essential protein, is retained repelled) and not lost to the dialysate (neutral stream). An important point is that the exclusion of albumin is representative of the response of other charged species in blood plasma. Further, this separation occurred without damage to components in the blood. No bright spots indicative of protein aggregates were observed.

Evaluation of Device Lifetime and Membrane Biofouling.

Using this single-electrode scheme, device lifetime was evaluated and the tendency for the membrane to foul. This evaluation consisted of two separate experiments—with and without contact of the membrane with blood plasma prior to IDZ formation. In the first experiment, the device was rinsed with buffer as described in the previous experiment, and then the solution in the channel was replaced with 0.05 mg/mL dye-linked albumin in undiluted blood plasma. The device was allowed to sit at room temperature with the membrane in contact with the plasma. A driving voltage (12.0 V) was applied intermittently (every 30 min) to determine if the IDZ would still form. The IDZ was stable over the longest times investigated (6 h). This result is significant because it indicates that the device (electrodes and membrane) do not undergo significant biofouling while the voltage source is off.

Importantly, it was expected that during operation the IDZ would continuously protect the membrane by preventing its contact with macromolecules in the blood. Therefore, the device lifetime was further tested in the absence of contact between the blood plasma and permselective membrane. This condition was accomplished as follows. First, the device was rinsed with 10.0 mM phosphate buffer, and the volumes in the reservoirs were adjusted to 40.0 µL (inlet) and 20.0 µL (both outlets). Second, a 30.0 V driving voltage was applied (single-electrode configuration) to initiate IDZ formation. Finally, the buffer solution in the inlet was replaced with 40.0 µL of 0.05 mg/mL dye-linked albumin in undiluted blood plasma. The volume of sample solution in the reservoirs was adjusted to 34.0 µL (inlet) and 14.0 µL (upper outlet) to generate flow from left to right. The volume in the neutral stream outlet was not altered. The driving voltage was adjusted to 40.0 V. Repulsion of the dye-linked albumin at the IDZ boundary was observed as the plasma entered the main channel. This observation indicates that contact between the blood plasma and the membrane was prevented. The separation was monitored for 12 h, and no instability of the IDZ occurred during this time (Supporting Information). At 5 h, the drying voltage was increased to 55.0 V (37.5%) to adjust the location of the IDZ boundary. At 12 h, the sharpness of the transition in fluorescence intensity at the IDZ boundary was reduced, which could be indicative of changes in the Nafion membrane. However, the separation persisted until the experiment was terminated. For an experiment in which a driving electrode was kept in contact with blood plasma, the operation time was reduced to 7 h, after which the electrode was fouled by a visible protein coating. This result underscores the importance of housing the driving electrode in the neutral stream and preventing contact with blood plasma, especially under an applied voltage.

Evaluation of the Output of the Neutral Stream.

Figure 6:
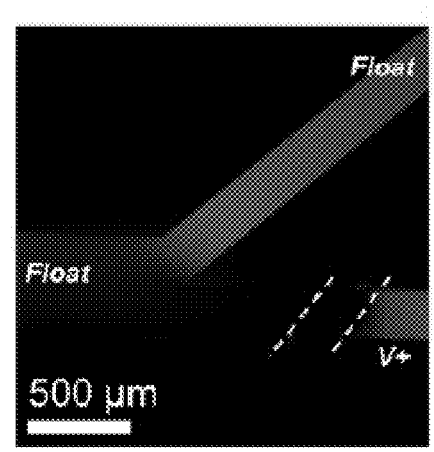
FIG. 6 shows fluorescence micrograph showing the location of BODIPY FL in undiluted blood plasma, wherein the BODIPY FL is depleted with 40.0 V driving voltage.

While fluorescently-tagged species indicate the general behavior of charged and neutral compounds in blood, a full characterization of the composition of the outlet streams is necessary to guide further development of this ICP-based separation as a method to source dialysate from blood. Importantly, some neutral compounds are carried into the charged stream by way of intermolecular interactions between these compounds and charged species present in plasma. FIG. 6 demonstrates this concept in that a neutral dye (1.0 µM BODIPY FL) undergoes depletion in blood plasma, whereas in model blood (FIG. 3A) it did not. This experiment was performed using the same protocol as was used to obtain the results shown in FIG. 5, but with the addition of 1.0 µM BODIPY FL in the blood plasma. Further, the flow rate (left to right, FIG. 6) and voltage were not adjusted after the initial addition of plasma to the inlet. The decreased flow rate and high voltage (40.0 V) are responsible for the observed extension of the depleted region upstream of the branching junction. An important consequence of the partial separation of neutral compounds from plasma is that the complexity of the neutral stream is reduced, which in turn simplifies its repurposing as dialysate. This fluid would be processed by flowing through a sorbent bed to yield purified water, followed by incorporation of additives (e.g., a bicarbonate source) currently employed in clinical practice to formulate dialysate.

Example 2

Evaluation of Device Lifetime and Membrane Biofouling.

Prior to experiment the channels were rinsed with 10 mM phosphate buffer solution. In this experiment, the rinsing phosphate buffer was then replaced with fresh 10 mM phosphate buffer and the reservoir volumes were adjusted to 40 µl (inlet) and 20 µl (both outlets). Second, 30.0 V was applied at neutral stream reservoir of the main channel versus the auxiliary channel (ground). Third, the buffer solution in the inlet was replaced with 35.0 µL of 0.05 mg/mL dye-linked albumin in undiluted blood plasma. Finally, the volume of sample solution in the reservoirs was adjusted to 34.0 µL (inlet) and 14.0 µL (upper outlet) to generate flow from left to right. Neutral stream outlet remained unchanged. The driving voltage was adjusted to 40.0 V. Repulsion of the albumin at the IDZ boundary was observed as the plasma entered the main channel. Outlet reservoir volumes were adjusted every 20 minutes by increments of 0.1 µL. The voltage was increased to 55.0 volts after first 5 hours to sustain stable IDZ.

Figure 8:
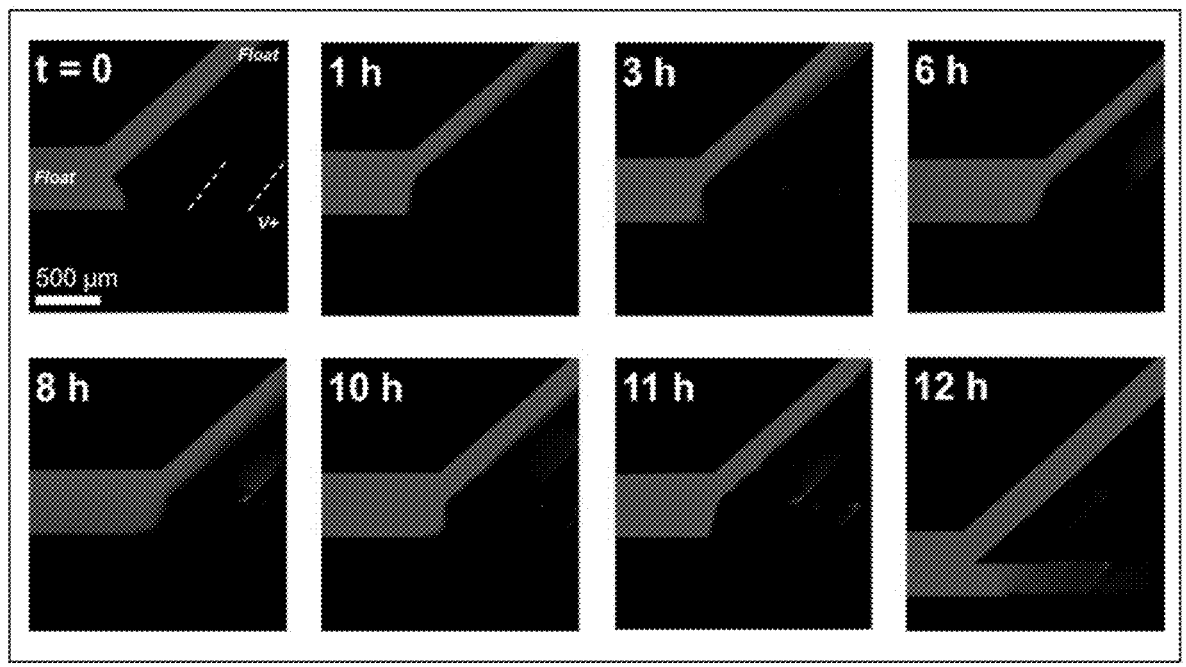
FIG. 8 shows fluorescence micrographs with the location of dye-linked albumin in undiluted blood plasma over 12 hours, where dye-linked albumin is redirected into the upper branched channel under an applied voltage and white dashed line represents Nafion membrane location in lower branch channel.
Figure 9:
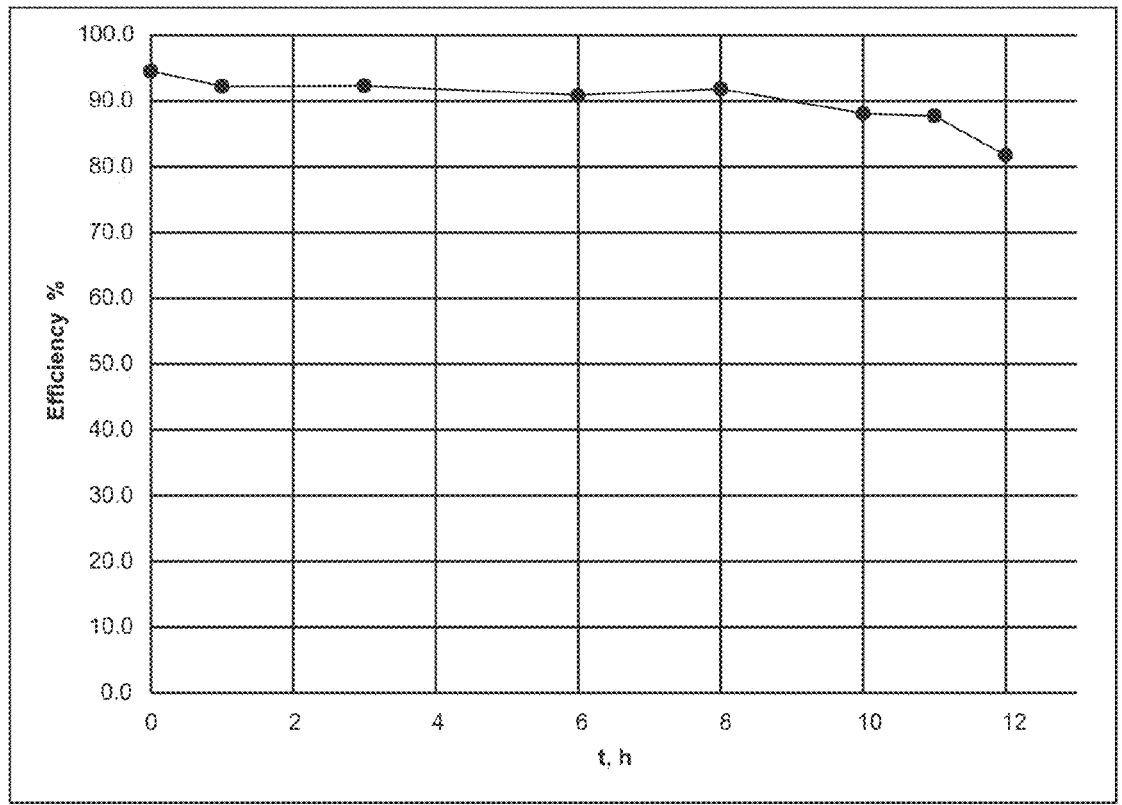
FIG. 9 shows evaluated separation efficiency of dye linked albumin in undiluted blood plasma over 12 hour period according to an embodiment of the invention.

FIG. 8 shows fluorescence micrograph showing the location of dye-linked albumin in undiluted blood plasma. The dye-linked albumin is redirected into the upper branched channel under an applied voltage. White dashed line represents Nafion membrane location in lower branch channel.

Separation efficiency was evaluated using mean fluorescence intensity measurements across the lower branched channel (0.2 mm after the Nafion membrane) and comparing it with intensity profile in the inlet segment of the main channel by using NIS software. The separation efficiency of >90.0% were maintained over the initial 9 hour period.

Example 3

Evaluation of Flow Vs Voltage Relationship: Run to Run Variance.

Figure 10:
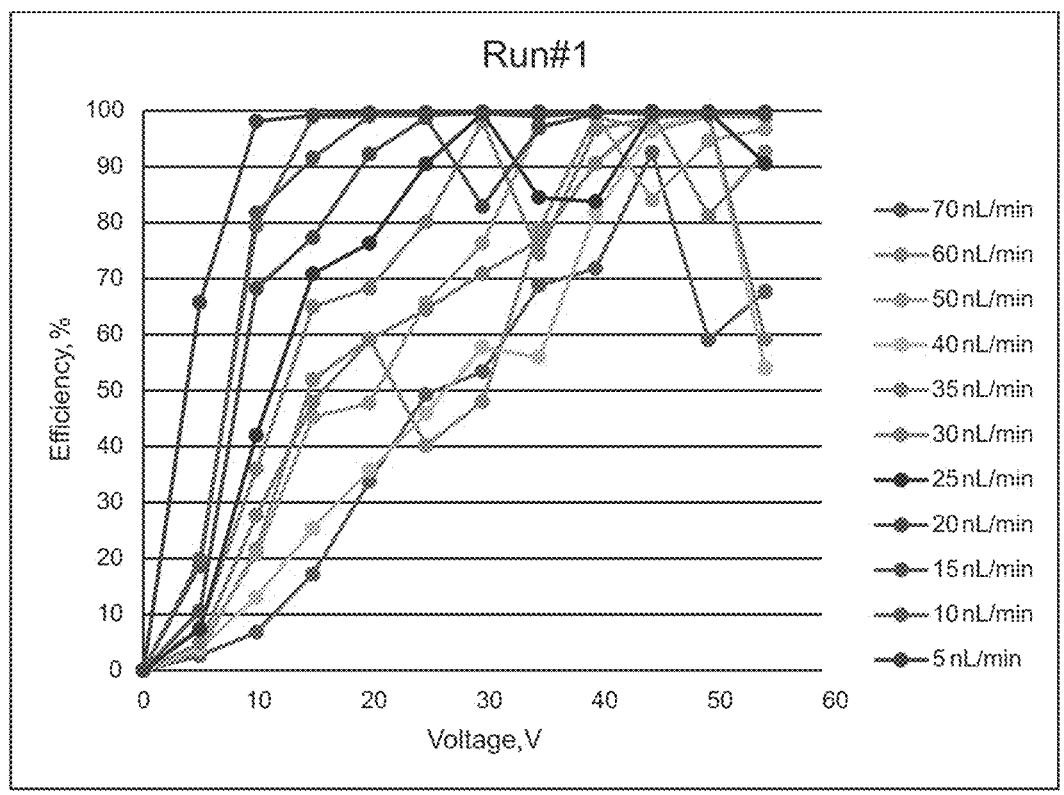
FIGS. 10-11 show evaluated separation efficiency of dye linked albumin at different flow rates and voltages applied at the branched microfluidic junction as described in Example 3.
Figure 11:
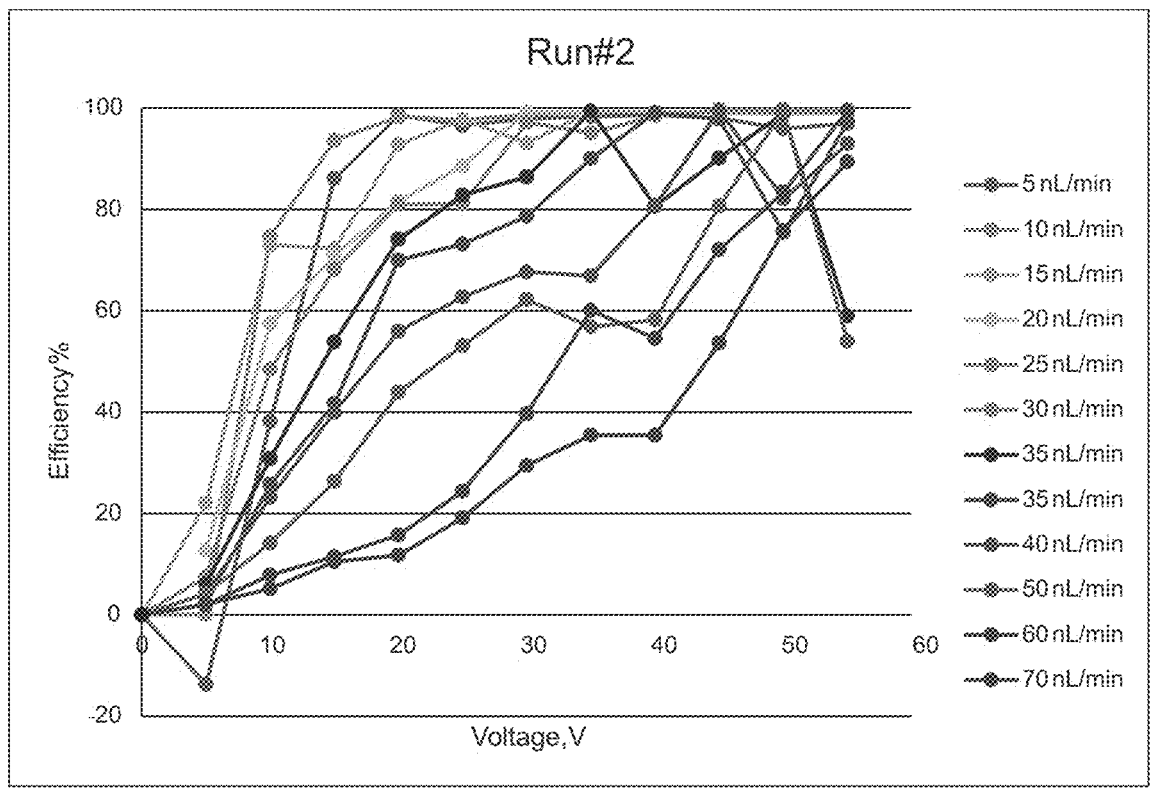

The microfluidic device was assembled according to Example 2. The Nafion membrane was located 0.320/0.440 mm from the junction in the neutral stream branch. Prior to the experiment, the channels were rinsed with 10 mM phosphate buffer solution. Undiluted blood plasma sample spiked with dye linked albumin was injected into the device using 0.50 mL Hamilton syringe with 1 mm PTF tubing. To control flow rate during the experiment, syringe pump was used. The voltage was increased every 1 minute after which fluorescence micrograph was taken and intensity profiles of neutral stream branch analyzed. The flow was then increased and allowed to equilibrate for 10 minutes and voltage sequence repeated. The tested flow rate range was from 5 to 70 nL/min, voltage range from 5.0 V to 55.0 V. In between runs, the flow rate was allowed to equilibrate for 30 minutes. Obtained data indicate that high separation efficiency can be achieved using low flow rates and low applied potential, <99% separation efficiency can be achieved by applying only 15.0 V driving voltage when the flow rate is 5 nL/min. To achieve similar separation efficiency while increasing the flow rate, the applied driving potential also must be increased (60 nL/min, 50.0 V, <99%). Results show that similar efficiency profile pattern can be observed from run to run using the same microfluidic device as depicted in FIGS. 10-11.

Example 4

Evaluation of Flow Vs Voltage Relationship on Separation Efficiency: Device to Device Variance.

The microfluidic device was assembled according to previously described methods. The Nafion membrane was located 0.670/0.900 mm from the junction in the neutral stream branch. Analogous to run to run variance evaluation experiment, prior to the experiment, the channels were rinsed with 10 mM phosphate buffer solution. Undiluted blood plasma sample spiked with dye linked albumin was injected into the device using 0.50 mL Hamilton syringe with 1 mm PTF tubing. To control flow rate during the experiment, syringe pump was used. The voltage was increased every 1 minute after which fluorescence micrograph was taken and intensity profiles of neutral stream branch analyzed. The flow was then increased and allowed to equilibrate for 10 minutes and voltage sequence repeated. The tested flow rate range was from 5 to 25 nL/min, voltage range from 5.0 V to 55.0 V.

Figure 12:
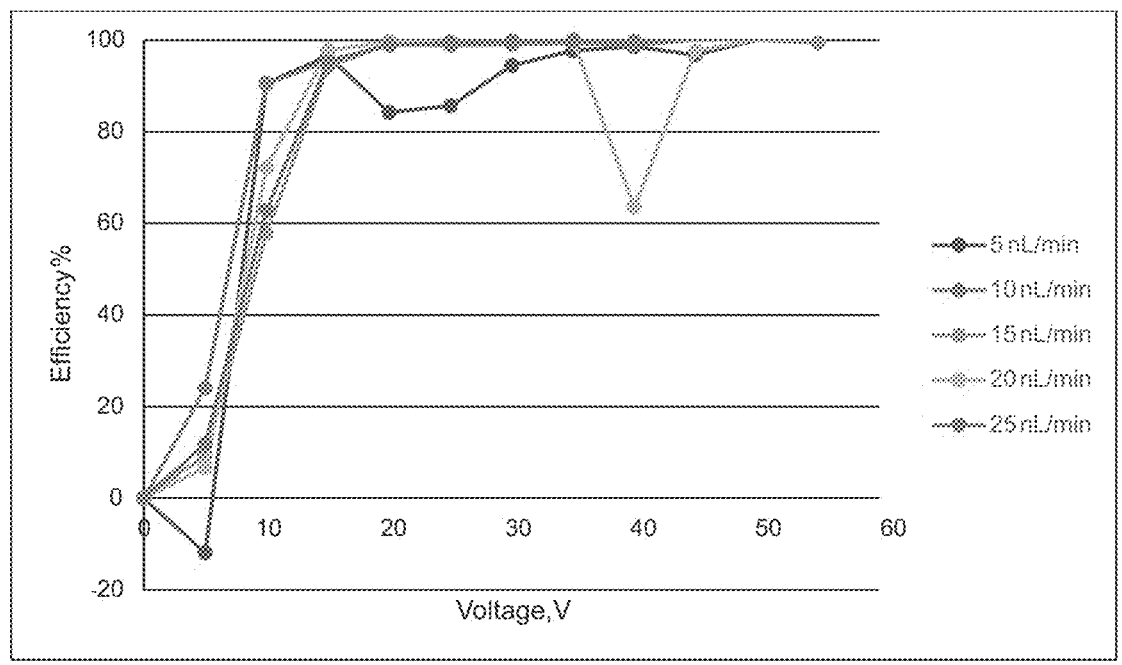
FIG. 12 shows flow vs voltage relationship on separation efficiency: device to device variance as evaluated and described in Example 4.

Results shown in FIG. 12 indicate that there is a significant influence on Nafion membrane location to separation efficiency. By locating the Nafion cut further into the channel, high efficiency separation can be achieved by using low flow rates. When higher flow rates are applied, ion depletion zone is unstable and the separation efficiency decreases.

Example 5

System Configuration Control Experiments:

The microfluidic device was assembled according to previously describe method. Nafion membrane distance from the junction was 1.0 mm. FIG. 5 shows the behavior of albumin (labeled with Texas Red) and uncharged dye (green, BODIPY FL) at an ion permselective junction when potential bias is applied. Fluorescence micrographs were taken simultaneously for both channels using NIS Nikon software Multichannel settings.

Figures 13A, 13C, 13E, 13G:
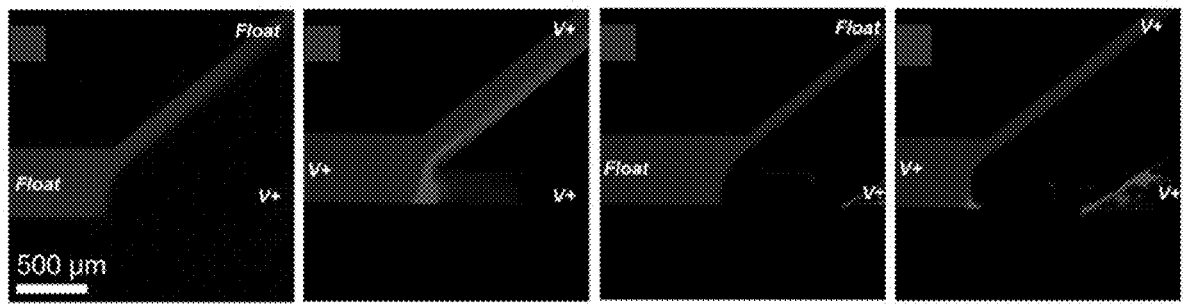
FIGS. 13A-13H show fluorescence micrographs depicting the location of dye-linked albumin in undiluted blood plasma, wherein the dye-linked albumin is redirected into the upper branched channel under an applied voltage
Figures 13B, 13D, 13F, 13H:
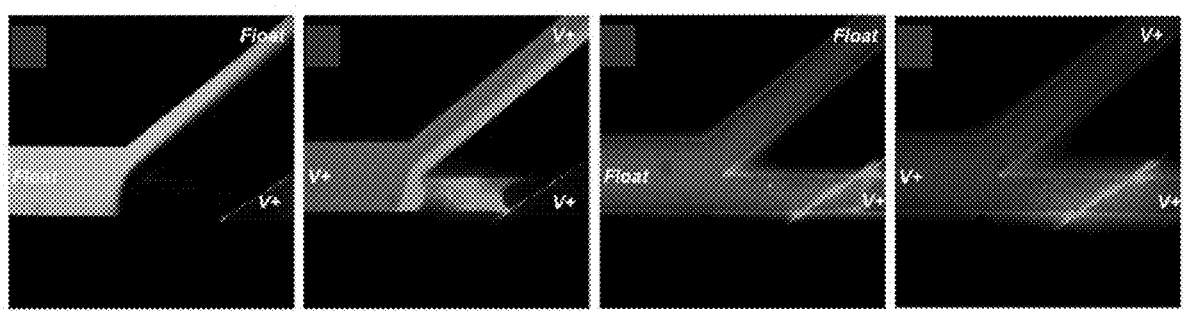

FIG. 13A-13B show the behavior of dye linked albumin (Texas Red) and uncharged dye (BODIPY FL) in undiluted blood plasma when 40.0 V potential is applied at the neutral stream outlet reservoir of the main channel versus the auxiliary channel (1 driving electrode system). Both albumin (Texas Red) and uncharged dye (BODIPY FL) were depleted and directed to upper branch channel. Similar behavior of albumin and uncharged dye can be observed using 3 driving electrode system, indicating that system configuration is not influencing the neutral BODIPY FL behavior in human blood plasma near the ion depletion zone.

The solution that models the pH and salinity of blood was used to confirm pervious findings. The solution contained 0.05 mg/mL dye-linked albumin (approx. 1.0% of the concentration of albumin in human blood) and 1.0 µM BODIPY in 50.0 mM NaCl, 5.0 mM KCl, and 20.0 mM carbonate at pH 7.4. When 40.0 V were applied at the neutral stream outlet reservoir of the main channel versus the auxiliary channel (ground), the albumin depleted (FIG. 13E), however uncharged dye showed no significant depletion behavior (FIG. 13F). Similarly using 3 electrode system configuration, only albumin showed significant depletion behavior (FIG. 13G-13H).

Example 6

Electrode Biofouling Experiment:

A voltammetric study of protein deposition on Pt working electrode was performed.

Experimental ICP Setup.

Prior to experiment the microfluidic device were rinsed with 10 mM phosphate buffer solution. Second, the buffer solution in the inlet was replaced with 60.0 µL of 0.05 mg/mL dye-linked albumin in undiluted blood plasma. The Pt working electrode was position in the main channel inlet. Finally, the driving voltage of 40.0 V were applied at the inlet reservoir of the main channel versus the auxiliary channel. The cyclic voltammogramm was recorded to evaluate plasma protein deposition on Pt working electrode before the experiment and 1, 3, 5, 7 hours after the beginning of experiment. The Pt driving electrode with protein deposits were gently rinsed with DDI before and after the voltammetric experiments for further ICP generation in microfluidic device.

Voltammetric Study.

The experiments were performed using Pine WaveDriver 20 Bipotentiostat/Galvanostat system (Durham, N.C., USA). The working Pt electrode was rinsed with DDI, followed by EtOH and dried under stream of nitrogen before use. The electrochemical cell consisted of Pt wire working electrode, Ag/AgCl/0.1 M KCl reference electrode and Pt wire auxiliary electrode. 10 mM fern ferrocyanide redox couple in 1.0 M KCl solution was used. Six cyclic voltamogramm segments were recorded. Initial and final potential of the sweep was −0.40 V, scan range −0.40 to +0.70 V. Sweep rate 50 mV/s. Initial current range 10 µA.

Figure 14:
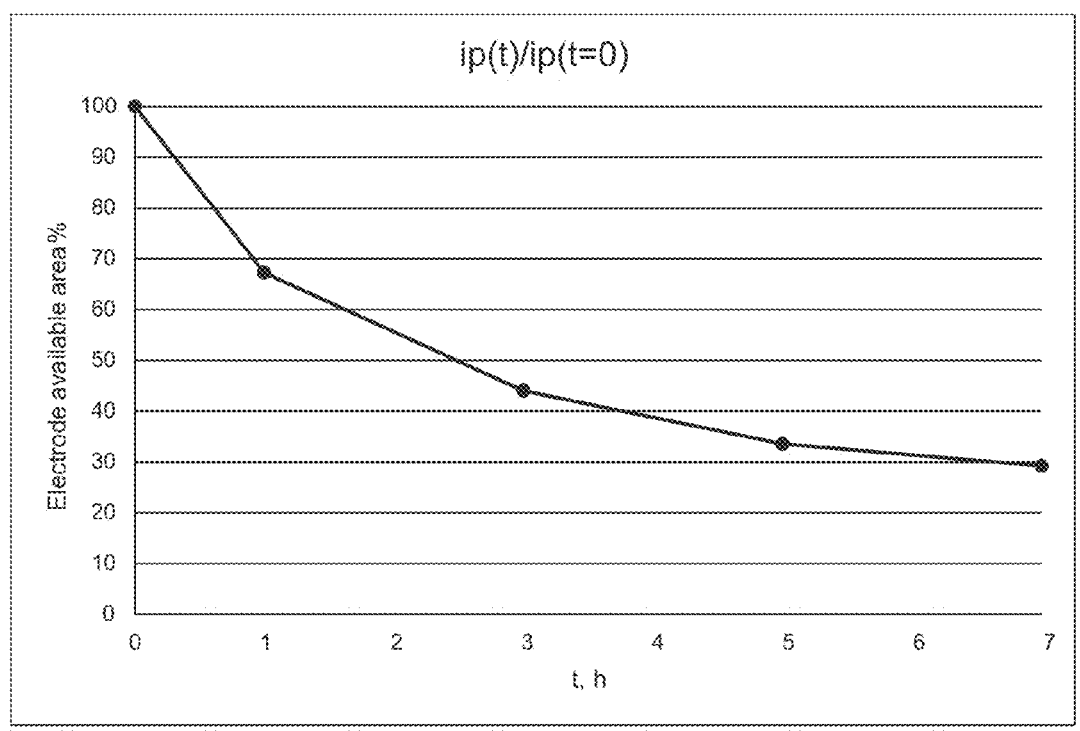
FIG. 14 shows available Pt driving electrode area % representing plasma protein deposition at the electrode as a function over time according to an embodiment of the invention.
Figure 15:
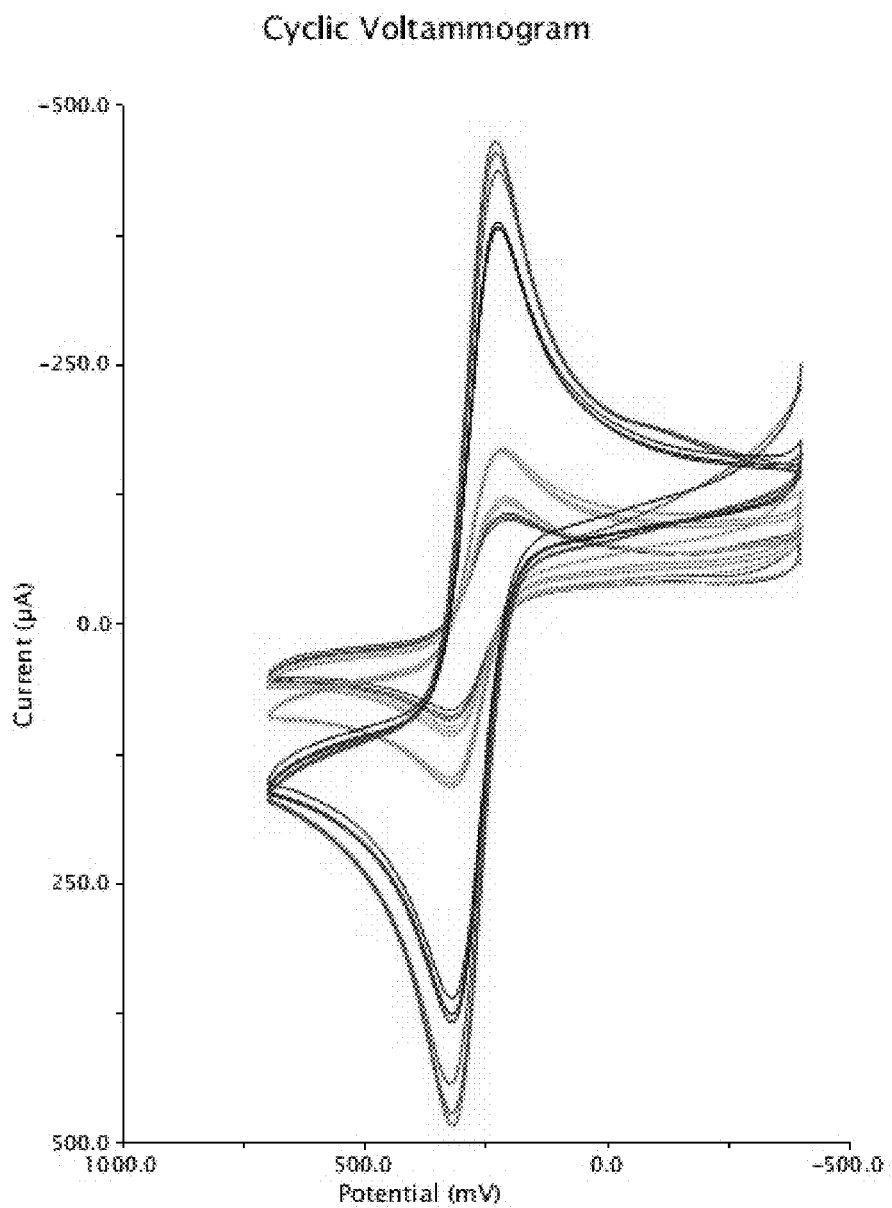
FIG. 15 shows cyclic voltammogram of fern ferrocyanide redox couple using Pt wire working electrode. The protein deposition influence is presented using voltammetric measurements after 1, 3, 5, 7 hours. All potentials are represented using Ag/AgCl/1 M KCl reference electrode.

Results presented in FIGS. 14-15 show that available electrode area % to drive to redox reaction is significantly decreasing over time. The protein deposition on electrode surface decrease the electrode active area by 70% in 7 hours.

Example 7

Membrane Resistance Measurements.

The microfluidic device was assembled according to previously described method. The microfluidic device was washed with 10 mM phosphate buffer for 48 hours prior to resistance measurements to condition the membrane. The total resistance of the system was measured using picoammeter (Keithley, Beaverton, Oreg.).

Microfluidic system setup was as follows: the channels were filled with 10 mM phosphate buffer solution, (flow rate 10 nL/min, syringe pump). Driving voltage of 40.0 V were then applied across the membrane and resistance measurements taken. The average total resistance of the phosphate buffer system was 6.3 MΩ over 1 hour period.

Further, the channels were filled with undiluted blood plasma (10 nL/min, syringe pump). To avoid plasma protein deposition on Nafion membrane and protein leak into the lower branched channel, the voltage source was kept on for continuous ion depletion. The total resistance of the undiluted blood plasma system remained stable over 1.5 hour period (average 2.64 MΩ) indicating that no significant membrane biofouling occurred during this period of time.

Example 8

Exemplary volumetric throughput of the device and dialysate consumption were quantitated and demonstrate the ability to reduce dialysate consumption through regeneration. In an exemplary clinical application of ICP-based separation there is a requirement for volumetric throughput, which is estimated here.

For this approach to become a practical means of obtaining patient-derived dialysate, the ICP-based separation requires considerable scaling. Hemodialysis treatment of a patient during a 3 h session at a medical center consumes 300-600 mL/min of dialysate, which if spread evenly over the week, is equivalent to 15-30 mL/min. A similar dialysate consumption rate was reported for a clinical trial of the WAK. This volumetric rate is not sustainable if sourced entirely from blood (the human body contains approximately 5 L of peripheral blood). Therefore, a reasonable path to applying this approach may employ slow-flow, or low-dialysate consumption hemodialysis in combination with in-line dialysate regeneration.

For example, dialysate regeneration resulting in a 95% volumetric recovery (i.e., 20-fold enrichment of waste) would reduce fluid consumed by dialysis to about 1.0 mL/min, which matches a healthy rate of urine production. This figure underscores the inefficiency of hemodialysis relative to a healthy human kidney. Such a dialysate consumption rate could be matched by 10,000 of the microscale devices claimed here if operated each at 0.1 µL/min in parallel. The volumetric flow rate of each device can be scaled up to reduce the total number of devices required. Importantly, this ICP-based approach itself could be employed to regenerate spent dialysate and reduce the rate of consumption.

While these estimates demonstrate that ICP-based separation can supply dialysate at a sufficient rate, they do not answer the question of whether such a volume can be sourced from blood. Patients suffering from kidney failure produce minimal quantities of urine, and instead of being excreted, the fluid is retained. Healthy human kidneys produce urine at a rate of 800 to 2000 mL/day, which is 0.56 to 1.39 mL/min. Upon comparison of these figures with the estimated rate of consumption above (0.134 to 0.267 mL/min), it becomes clear that there is excess fluid that can be spared for the generation of dialysate.

Example 9

Additional evaluation of the ability to use ICP to continuously separate charged species from an aqueous solution in a branched, flow-through microfluidic device were conducted. The need for separating and enriching neutral analytes in aqueous solutions by conferring a pseudo-charge to neutral compounds via their partition into an ionic micellar phase were evaluated. The use of ICP based separation as shown in FIG. 2 was further evaluated.

Adding ionic surfactants (such as anionic, cationic or zwitterionic surfactants) above the critical micelle concentration (CMC) has shown to be an effective technique in capillary electrophoresis for neutral compound separation. In micellar electrokinetic capillary chromatography (MEKC), formed micelles act as a pseudo-stationary phase and interact with analytes based on their hydrophobicity. In this scenario, compounds that are not ionized under experimental conditions can be incorporated into the micelle and then electrophoretically separated using the charge of the micelles. The data show that in combination with ICP, this approach permits the electrokinetic separation of neutral species to an extent dependent upon the partition of analyte into the micelle, and the concentration ratio of micelle and analyte to create a micelle-analyte pair. The data quantifies the charged micelle-analyte pair separation efficiency as a function of flow rate and applied voltage. Critical to the practical application of this method, it has been demonstrated that neutral analyte separation at global concentrations of surfactants below the CMC by locally enriching surfactants to form micelles at the IDZ boundary. Collectively, these results demonstrate the capabilities of a new technique for focusing of neutral targets—continuous micellar electrokinetic separation (CMEKS).

Chemicals.

Texas Red and CellTracker Green BODIPY dye were obtained from Molecular Probes (Eugene, Oreg.). Sodium dodecylsulfate (SDS), an anionic surfactant, Nafion perfluorinated resin (20 wt % solution in lower aliphatic alcohols) and Pluronic F-108 (poly(ethylene glycol)-block-poly(propylene glycol) were purchased from Sigma-Aldrich, (St. Luis, Mo.). Platinum electrodes (99.95%) were purchased from Strem Chemicals (Newburyport, Md.). All solutions were made with reagent grade chemicals (Fisher Scientific, Waltham, Mass.) and diluted with double deionized water (18.2 MΩ·cm, Sartorius Arium Pro, Göttingen, Germany) before use.

Critical Micelle Concentration (CMC) Determination.

Conductivity study was performed to verify the critical micelle concentration of SDS in 10.0 mM sodium phosphate buffer (pH 7.4, 22° C.) with and without adding BODIPY. The conductivity was measured using Orion Star A215 pH/Conductivity meter (Thermo Scientific, Waltham, Mass.).

A 25.00 mL solution of SDS (20.0 mM) in sodium phosphate buffer (10.0 mM, pH 7.4, 22° C.) was consecutively diluted under vigorous stirring (1200 rpm). Measurements were taken every minute after each change in concentration. The CMC in sodium phosphate buffer of SDS is 4.53±0.03 mM.

Device Fabrication.

The microfluidic devices were fabricated using standard photolithography processes.[2] Channel molds were patterned using negative photoresist (SU-8 2050, Microchem Corp., Westborough, Md.) on Si substrate. Poly(dimethylsiloxane) (PDMS) (Sylgard 184 elastomer kit, Dow Corning Corp., Midland, Mich.) was used for device fabrication. The separation channel was 46.0 μm tall and 10.0 mm long, having 500 μm-wide main channel that branched into two channels (each 250 μm wide for 1:1 aspect ratio between upper and lower branches). A second channel (auxiliary channel) 10.0 mm long and 500 μm wide was located parallel to the separation channel at a distance of 300 μm. A 4.0 mm-diameter biopsy punch was used to create the inlet and outlet reservoirs, unless noted otherwise. A mechanical incision was made using a scalpel blade across the lower branch and auxiliary channel, and subsequently filled with 3.0 μL of Nafion. The membrane was then cured at 95° C. for 10 min. Excess Nafion was removed by applying and peeling away low residue tape. The PDMS layer and glass slide were treated with air plasma (PDC-001, Harrick Plasma, Ithaca, N.Y.) for 60 s (medium RF power) and then bonded together. All microfluidic devices were rinsed with double deionized water and coated with Pluronic (3.0 μM in 10.0 mM phosphate buffer) for at least 18 h. The Pluronic solution was used to suppress the electroosmotic flow. The microfluidic devices were rinsed with 20.0 mM SDS solution for one hour before use to ensure uniform wall charge regardless of the SDS concentration employed in the experiment. Then just before use, the device was rinsed with 10.0 mM sodium phosphate buffer (pH 7.4) for 15 min to remove the 20 mM SDS. In each experiment, the driving voltage was applied between the outlet of the lower branch (V+, Figure S2) and both ends of the auxiliary channel (Gnd, Figure S2). Microfluidic devices with high aspect ratio between the upper and lower branches were used.

The first step was to characterize the behavior of charged (red, 1.0 μM Texas Red) and neutral (green, 50 μM BODIPY) species in ICP based separation in the absence of surfactant. The device was rinsed with 10.0 mM sodium phosphate buffer (pH=7.4) for 15 minutes. The buffer in the inlet reservoir was then replaced with 35.0 μL of 0.05 mM BODIPY and 1.0 μM Texas red solution in 10.0 mM sodium phosphate buffer. Then, the volume in the outlet reservoirs was adjusted to 20.0 μL to generate pressure driven flow of the solution in the main channel. Finally, a driving voltage of 60.0 V was applied. Fluorescence micrographs were taken 5 min after the driving voltage was applied.

Figure 16A:
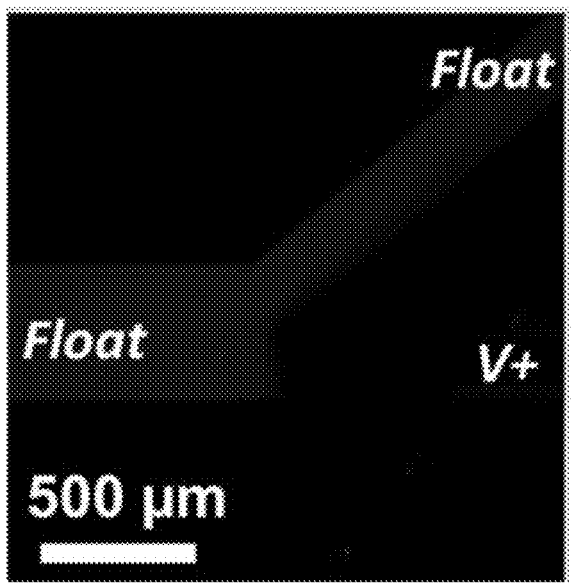
FIGS. 16A-16B show fluorescence micrographs of the location of Texas red (FIG. 16A) and BODIPY dyes (FIG. 16B), which are both representative of charged and neutral species.
Figure 16B:
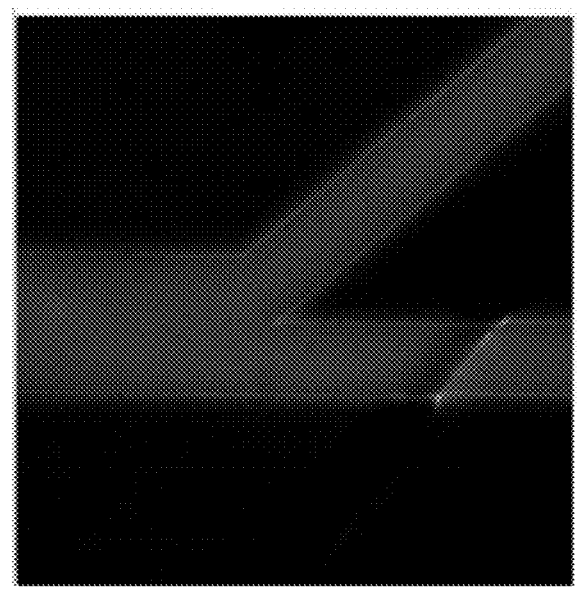

FIGS. 16A-16B show the behavior of charged and neutral species at the ion permselective junction in a sodium phosphate buffer solution (10.0 mM, pH 7.4). An IDZ formed immediately after applying a 60.0 V driving voltage, where charged species, represented by Texas red, were re-directed to the upper branch (FIG. 16A), while neutral species (BODIPY) were unaffected (FIG. 16B). These result confirm that neutral species are not deflected by the IDZ in the absence of surfactant.

Surfactant Influence on Neutral Analyte Separation by ICP.

Next, the impact on neutral species separation of a surfactant present at several distinct concentrations was evaluated. After rinsing, the buffer in the inlet reservoir was replaced with 35.0 μL of SDS solution (0.0-20.0 mM) and 50 μM BODIPY in sodium phosphate buffer (10.0 mM, pH 7.4). Then, the volume in the outlet reservoirs was adjusted to 20.0 μL to generate pressure driven flow of the solution in the main channel. Finally, a driving voltage of 60.0 V was applied. Fluorescence micrographs were taken 5 min after driving voltage was applied and IDZ formation occurred. The device was rinsed thoroughly with 10.0 mM phosphate buffer, re-coated for 15 min using 20.0 mM SDS solution in 10.0 mM sodium phosphate buffer, re-rinsed with phosphate buffer (10.0 mM, pH 7.4) in between trials and imaged to ascertain the background fluorescence intensity of the channel walls and to account for residual BODIPY adsorption. Mean fluorescence intensity across the lower branch of microfluidic device was measured 300 μm downstream from the ion selective membrane and used for quantitative analysis. All fluorescence intensities were background subtracted. Separation efficiency (SE) was calculated by comparing this intensity (I) to the initial intensity prior to initiation of ICP ($I_0$) such that $SE=100\%(1-I/I_0)$.

Figure 17A:
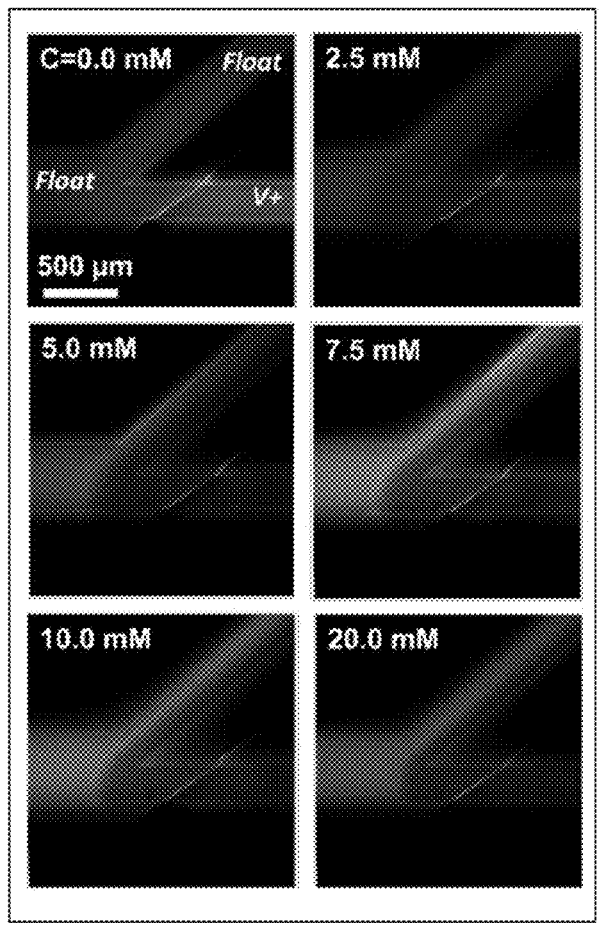
FIG. 17A shows fluorescence micrographs showing the location of neutral species (BODIPY) in solutions having distinct SDS concentrations under applied voltage of 60.0 V.
Figure 17B:
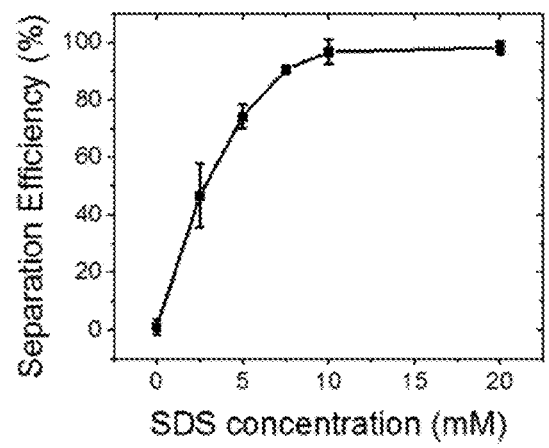
FIG. 17B shows the SDS concentration compared to separation efficiency.
Figure 17C:
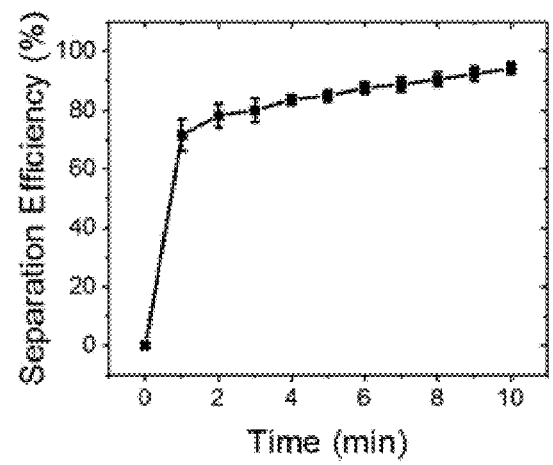
FIG. 17C shows the neutral species separation efficiency at different time points after initiation of ICP using 10.0 mM SDS in 10.0 mM phosphate buffer at flow rate of 60 nLmin−1, and under applied voltage of 60.0 V. Error bars represent the standard deviation for three replicates.

The results are shown in FIGS. 17A-17C showing that increasing surfactant concentration above the CMC results in neutral species repulsion from the IDZ and into the upper branch. FIG. 17A shows images of the separation of neutral species (BODIPY, at an initial concentration of 50 μM) as a function of the concentration of the anionic surfactant, sodium dodecyl sulfate (SDS), under an applied voltage of 60.0 V. The results show that modest separation (50%) is achieved by using SDS concentrations below 5.0 mM (CMCSDS=4.53±0.03 mM, 10.0 mM sodium phosphate buffer, pH 7.4 (see SI)). In contrast, separation efficiencies above 90% can be achieved by using SDS concentrations above 7.5 mM, reaching a maximum efficiency at 10.0 mM SDS (>95%) (FIG. 17B). These results are significant because they highlight the utility of micelles for electrokinetic focusing of neutral species and demonstrate that onset of separation occurs near the CMC.

Using phosphate buffer solution containing 10.0 mM SDS, it was further investigated the dependence of flow rate (40-70 nL/min) and applied driving voltage (10.0-100.0 V) on separation efficiency. For these sets of experiments, a 1.0 mm in diameter biopsy punch was used to create the device inlet reservoir. A 10.0 mM SDS solution in sodium phosphate buffer (10.0 mM, pH 7.4) spiked with 0.050 mM BODIPY was continuously flowed into the device using a 0.50 mL Hamilton syringe through a 1.0 mm outer diameter PTF tubing. After establishing a flow rate of 50 nL min$^{-1}$ a driving voltage of 100.0 V was applied. After establishing a stable flow rate, the voltage was decreased by 10.0 V increments at 1 min intervals. After full voltage sequence, the device was thoroughly rinsed for 15 minutes using phosphate buffer solution (10.0 mM, pH=7.4), and imaged to obtain background fluorescence intensity of the channel walls. Further the background subtracted fluorescence intensity was used for separation efficiency quantification. These experiments were repeated three times each at flow rates of 40, 60 and 70 nL min$^{-1}$.

FIG. 17C shows that at flow rates 40-60 nL min$^{-1}$ moderate separation efficiencies can be achieved by applying voltages above 60.0 V, and maximum separation efficiency (>95%) can be achieved at 100.0 V. However, by increasing the time interval between voltages from 1 min to 10 min, the separation efficiency can be increased to >95% using flow rate of 60 nL min$^{-1}$ and applying driving voltage of 60.0 V. Thus, this flow rate and voltage were employed in all following experiments, which demonstrate the neutral guest (BODIPY) separation at surfactant concentrations below the CMC (in high aspect ratio devices).

Analyte Concentration Influence on Separation Efficiency.

To ensure high separation efficiency, the concentration of the micelles must be sufficiently high to avoid saturation with the neutral species. After treatment with SDS and rinsing with phosphate buffer, the buffer in the inlet reservoir was replaced with 35.0 μL of SDS solution (10.0 mM) in sodium phosphate buffer (10.0 mM, pH 7.4) with BODIPY at 0.05, 0.10, 0.50, 1.0 or 5.0 mM. Then, the volume in the outlet reservoirs was adjusted to 20.0 μL to generate pressure driven flow of the solution in the main channel. Finally, a driving voltage of 60.0 V was applied. Fluorescence micrographs were taken 5 min after the driving voltage was applied and IDZ formation was observed. The device was rinsed 3 times with 10.0 mM phosphate buffer, re-coated for 15 min using 20.0 mM SDS solution in 10.0 mM sodium phosphate buffer, and imaged to obtain background fluorescence intensity of the channel walls in between the trials. Separation efficiency was calculated as described in the preceding paragraphs.

Figures 18A, 18B, 18C:
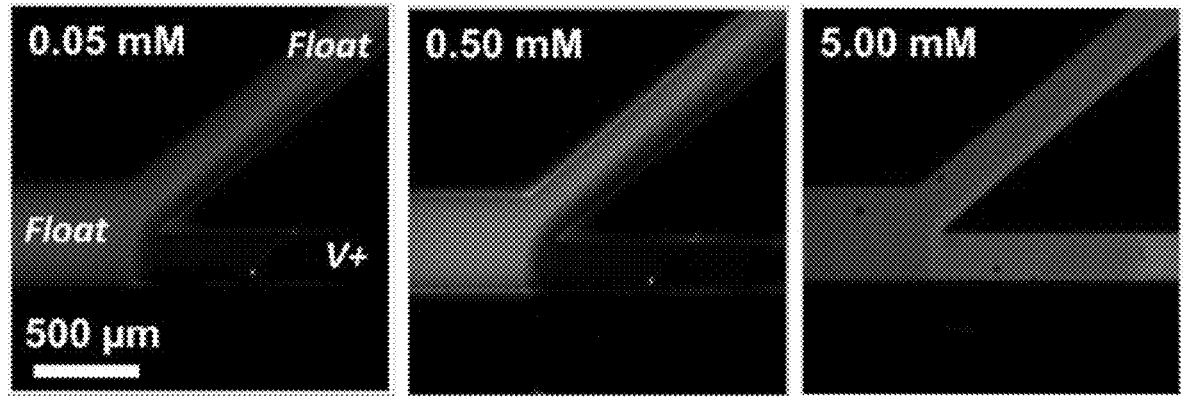
FIGS. 18A-18C show fluorescence micrographs showing the separation of a neutral dye (BODIPY) at three distinct concentrations (FIG. 18A) 0.05, (FIG. 18B) 0.50 and (FIG. 18C) 5.0 mM, all in 10.0 mM SDS (10.0 mM phosphate buffer) solution. Micrographs were obtained 5 min after applying 60.0 V driving voltage.
Figure 18D:
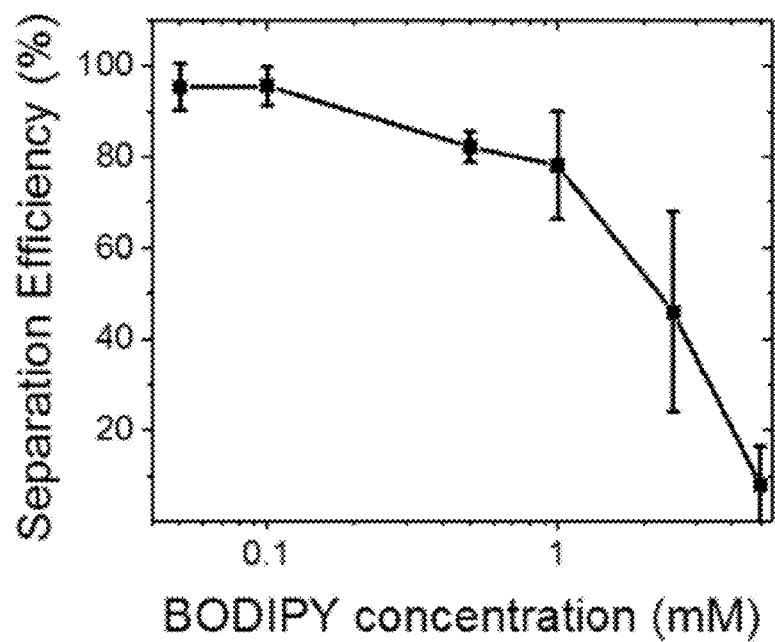
FIG. 18D shows a plot of separation efficiency as a function of BODIPY dye concentration for the conditions employed in (a-c).

FIG. 18 demonstrates the neutral species separation efficiency based on neutral species concentration while at a constant surfactant concentration (10.0 mM SDS). In the case where neutral analyte concentration is lower than that of the surfactant, the separation efficiency is as high as 95% (FIGS. 18A-18C). However, when neutral species concentration approaches or surpasses the surfactant concentration, the micelles become saturated with the neutral species and are unable to further accept the analyte, resulting in the rapid decrease of separation efficiency (FIG. 18C). Additionally, high neutral analyte concentration (>1.0 mM BODIPY) can cause precipitation, which contributed to higher standard deviations in separation efficiency at those concentrations. FIG. 18D shows a plot of separation efficiency as a function of BODIPY dye concentration for the conditions employed in (FIGS. 18A-18C). Error bars represent the standard deviation for three replicates.

Separation of Neutral Species Bound to Micelles Formed Locally by Enrichment of Surfactant.

To demonstrate that CMEKS is effective at global concentrations of surfactant below the CMC, neutral analyte separation in devices having a high aspect ratio between the upper and lower branches were evaluated. For these experiments, a 1.0 mm-diameter biopsy punch was used to create the device inlet reservoir. A 10.0 mM SDS solution in sodium phosphate buffer (10.0 mM, pH 7.4) spiked with 0.050 mM BODIPY was continuously flowed into the device using a 0.50 mL Hamilton syringe and 1.0 mm outer diameter PTF tubing. After establishing a flow rate of 60 nL min$^{-1}$ a driving voltage of 60.0 V was applied. A series of micrograph image were acquired over a period of 25 min (images taken at 1, 3, 5, 10, 15, 20, and 25 min) after the start of the experiment. The device was thoroughly rinsed with 10.0 mM phosphate buffer for 15 minutes, and imaged to obtain background fluorescence intensity of the channel walls. Fluorescence intensity profiles were measured axially along the separation channel and extending across the IDZ boundary (at least 550 μm). All fluorescence intensities were background subtracted.

Figure 19C:
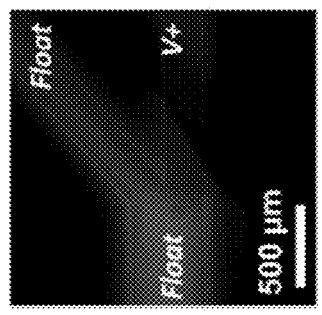
FIGS. 19A-19C show fluorescence micrographs showing BODIPY enrichment in the presence of 1.0 mM SDS in (FIG. 19A) 1:9, (FIG. 19B) 1:4 and (FIG. 19C) 1:1 aspect ratio devices in 10.0 mM phosphate buffer solution. Fluorescence micrographs were taken 20 min after applying 60.0 V driving voltage, flow rate 60 nL min−1.
Figure 19B:
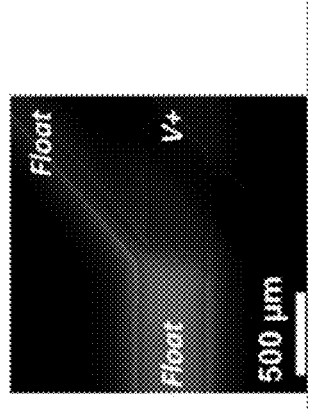
Figure 19A:
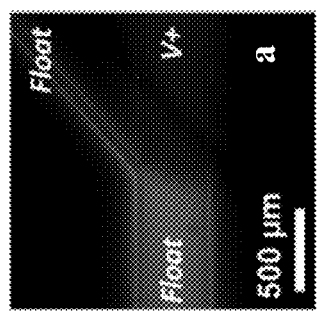
Figure 19F:
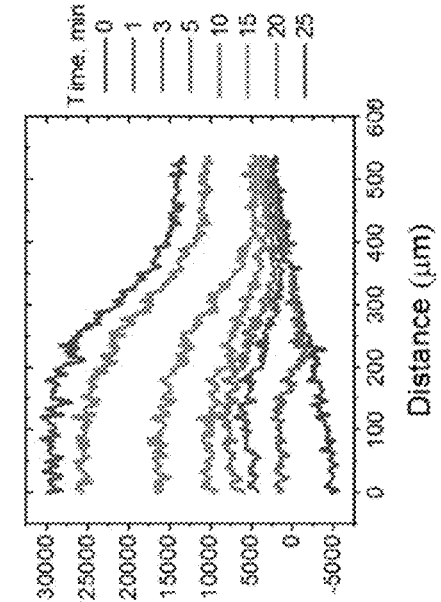
FIGS. 19D-19F show fluorescence intensity profiles across the IDZ boundary for (FIG. 19D) 1:9, (FIG. 19E) 1:4, and (FIG. 19F) 1:1 ratio microfluidic devices.
Figure 19E:
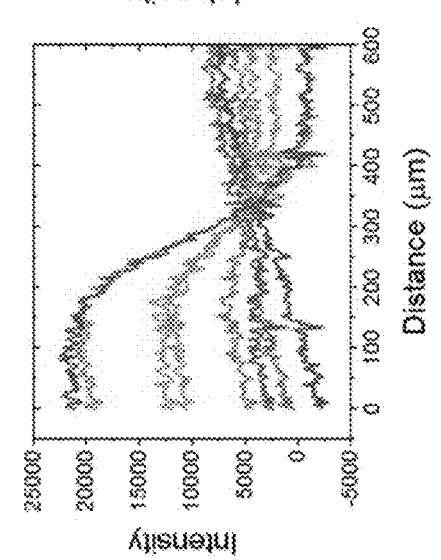
Figure 19D:
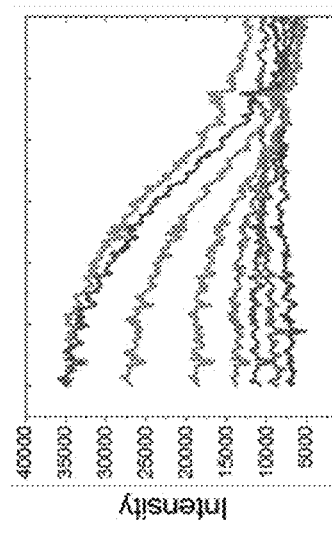

It was hypothesized that over time, SDS would enrich, near to the IDZ, from below to above the CMC. Data for FIG. 19 demonstrate intensity profiles across the IDZ boundary in three devices with varying ratio of upper branch and lower branch widths (1:9, 1:4, and 1:1, respectively) as a function of time. These results demonstrate that by using high aspect ratio devices (1:9 and 1:4), surfactant (SDS, 1.0 mM) present at a global concentration well below the CMC, exhibits an ability to encapsulate and separate BODIPY to an increasing degree over time. We attribute this behavior to gradual accumulation of SDS upstream of the IDZ boundary and the local formation of analyte-micelle pairs. By using high aspect ratio devices, separation efficiencies >90% can be achieved in 20 min (FIGS. 19A, 19B, 19D, 19E). However, only modest local enrichment and separation of neutral species are achieved using 1:1 ratio device (FIG. 19C).

The results show that electrokinetic separation of neutral species is achieved by using charged micelles in combination with ICP. Importantly, >95% separation efficiency can be achieved (in a device with a 1:1 branching ratio) while using surfactant concentrations above the CMC. In addition, it is demonstrated that high micelle concentration ensures high neutral analyte separation efficiency until the micelles become saturated and can no longer accept the neutral analytes. Local enrichment of surfactant near the IDZ allows for local micelle formation, thus neutral species separation can be achieved using low global surfactant concentrations. Further, in analytical applications, the specificity of certain micelles to bind targeted compounds can be leveraged to tailor separations. The preliminary findings presented here underscore the potential broad applicability of CMEKS.

Beneficially, the micelle-based methods can be employed for dialysate regeneration. The micelles can aid in removal of neutral (uncharged) waste from spent dialysate. This uncharged/neutral waste would, in the absence of micelles, not be separated from spent dialysate by ICP.

All publications and patent applications in this specification are indicative of the level of ordinary skill in the art to which this invention pertains. All publications and patent applications are herein incorporated by reference to the same extent as if each individual publication or patent application was specifically and individually indicated by reference. The disclosure of each reference set forth herein is incorporated herein by reference in its entirety.

The invention has been described with reference to various specific and preferred embodiments and techniques. However, it should be understood that many variations and modifications may be made while remaining within the spirit and scope of the invention.

What is claimed is:
1. A method for hemodialysis comprising:
removing neutral compounds from blood plasma of a subject in need of hemodialysis by ion concentration polarization;
obtaining fluid from the blood plasma containing the neutral compounds to source as a subject-derived dialysate; and
using the dialysate to accept metabolic waste during hemodialysis.

2. The method of claim 1, wherein the neutral compounds comprise water and small neutral molecules, and wherein the removal of neutral compounds by ion concentration polarization generates two streams from the blood plasma and is applied to the blood plasma at a rate of about 0.01 to about 50 mL/minute.

3. The method of claim 2, wherein the first stream is a charged stream that is recombined with cell containing fraction of the subject's blood, and wherein the second stream is a neutral stream comprising the fluid of the subject-derived dialysate.

4. The method of claim 1, wherein the ion concentration polarization takes place in a branched microchannel of a device comprising a membrane.

5. The method of claim 4, wherein the device is a branched, flow-through microfluidic device, and wherein the membrane is a nanoporous membrane with fixed charges along a pore surface.

6. The method of claim 1, further comprising flowing a surfactant into the device at an inlet to remove neutral compounds from the subject-derived dialysate.

7. The method of claim 1, wherein the ion concentration polarization selectively separates neutral compounds from charged compounds from the blood plasma, and herein the method further comprises forming an ion depletion zone for the continuous separation of the neutral compounds from the blood plasma, and wherein the ion depletion zone protects the membrane from biofouling and damage.

8. The method of claim 1, wherein at least 95% of protein including albumin content of the plasma is retained by the method and not lost to the dialysate.

9. The method of claim 1, wherein the ion concentration polarization selectively separates components from the blood plasma by charge and without relying on component size, density and/or molecular recognition.

10. The method of claim 1, further comprising contacting the dialysate with a purification media and/or incorporating hemodialysis additives.

11. A device for use with the treatment of a bodily fluid, comprising:
    a microfluidic member including an inlet channel terminating at a junction including a first branch and a second branch extending from the junction; and
    a charged ion permselective membrane positioned generally at or near the junction, said ion permselective membrane selected to direct charged particles into the first branch and substantially neutral fluid into the second branch;
    wherein the substantially neutral fluid is used as a natural dialysate for the treatment of the bodily fluid.

12. The device of claim 11, further comprising a second junction extending in a treatment channel wherein the first branch and the second branch are recombined.

13. The device of claim 11, wherein the treatment channel comprises an inner channel including the fluid with charged particles and an annular channel including the substantially neutral fluid and generally surrounding the inner channel, and wherein the inner and annular channels separated by a treatment membrane, wherein the treatment membrane is a dialysis membrane comprising a biocompatible material about 100 nm to 1.0 mm thick traversed by pores with a monodisperse or polydisperse distribution of diameters such that species having a molecular weight below about 3,000 Da, about 10,000 Da, about 30,000 Da, or about 60,000 Da are permitted through.

14. The device of claim 11, wherein the outer wall of the treatment channel comprises a capacitor plate, and/or wherein the ion permselective membrane is a nanoporous membrane having fixed charges along a porous surfaces, and/or wherein the membrane preferably comprises a Nafion membrane.

15. The device of claim 11, wherein the microfluidic member comprises:
    a. PDMS; or
    b. glass.

16. The device of claim 11, further comprising a coating on the interior of the microfluidic member to mitigate fouling, and/or one or more in-line quality control members positioned in the microfluidic member.

17. The device of claim 16, wherein the one or more in-line quality control members comprise sensors for sensing an aspect of the fluid passing therethrough, and wherein the sensors comprise:
    a. a glucose sensor; or
    b. a blood urea nitrogen sensor.

18. The device of claim 11, further comprising a transmitter for transmitting the information related to the one or more in-line quality control members.

19. The device of claim 11, further comprising an intelligent control, communication component, communications module or combinations thereof.

20. The device of claim 11, wherein the first branch and the second branch have a different size.

21. A method for treating kidney disease by hemodialysis, wherein the treatment comprises:
    providing a subject in need of hemodialysis with a branched, flow-through microfluidic device according to claim 11;
    optionally priming the device with a buffer;
    applying a charge to the device;
    separating neutral compounds from charged compounds in the subject's blood plasma at a rate of about 0.01 to about 50 mL/minute to generate two streams by ion concentration polarization, wherein the first stream is a neutral stream and the second stream is a charged stream;
    generating a fluid dialysate comprising the neutral stream from the subject's blood plasma; and
    contacting the dialysate and the second stream with a hemodialysis membrane to accept metabolic waste from the subject in need thereof.

22. The method of claim 21, wherein the charged stream is recombined with a cell containing fraction of the subject's blood.

23. The method of claim 21, wherein the device forms an ion depletion zone for the continuous separation of the neutral compounds from the blood plasma, and wherein the ion depletion zone protects the membrane from biofouling and damage.

24. The method of claim 21, wherein at least 95% of protein including albumin content of the plasma is retained in the second stream and not lost to the first stream.

25. The method of claim 21, further comprising contacting the dialysate with a purification media and/or incorporating hemodialysis additives comprising at least a bicarbonate source.

26. The method of claim 25, wherein the dialysate is purified by flowing through a sorbent bed to yield purified water before optionally incorporating hemodialysis additives.

27. The method of claim 21, further comprising flowing a surfactant to contact the neutral stream to form micelles to bind to neutral compounds.

* * * * *